US010174018B2

(12) United States Patent
He

(10) Patent No.: US 10,174,018 B2
(45) Date of Patent: Jan. 8, 2019

(54) PROTEIN KINASE INHIBITORS

(71) Applicant: Princeton Drug Discovery Inc, Monmouth Junction, NJ (US)

(72) Inventor: Kan He, Princeton, NJ (US)

(73) Assignee: Princeton Drug Discovery Inc, Monmouth Junction, NJ (US)

( * ) Notice: Subject to any disclaimer, the term of this patent is extended or adjusted under 35 U.S.C. 154(b) by 0 days.

(21) Appl. No.: 15/839,332

(22) Filed: Dec. 12, 2017

(65) Prior Publication Data

US 2018/0099960 A1 Apr. 12, 2018

Related U.S. Application Data

(60) Provisional application No. 62/539,785, filed on Aug. 1, 2017, provisional application No. 62/433,410, filed on Dec. 13, 2016.

(51) Int. Cl.
*A61K 31/506* (2006.01)
*C07D 417/14* (2006.01)
*A61P 37/00* (2006.01)
*A61P 25/28* (2006.01)
*A61P 35/02* (2006.01)
*A61P 35/00* (2006.01)
*A61K 45/06* (2006.01)
*C07B 59/00* (2006.01)
*C07D 417/12* (2006.01)

(52) U.S. Cl.
CPC .......... *C07D 417/14* (2013.01); *A61K 31/506* (2013.01); *A61K 45/06* (2013.01); *A61P 25/28* (2018.01); *A61P 35/00* (2018.01); *A61P 35/02* (2018.01); *A61P 37/00* (2018.01); *C07B 59/002* (2013.01); *C07D 417/12* (2013.01); *C07B 2200/05* (2013.01)

(58) Field of Classification Search
CPC ........................... A61K 31/506; C07D 417/12
USPC .......................................... 514/256; 544/327
See application file for complete search history.

(56) References Cited

U.S. PATENT DOCUMENTS

| | | | |
|---|---|---|---|
| 6,596,746 B1 | 6/2003 | Das et al. |
| 6,706,717 B2 | 3/2004 | Barrish et al. |
| 7,125,875 B2 | 10/2006 | Das et al. |
| 7,153,856 B2 | 12/2006 | Barrish et al. |
| 7,189,854 B2 | 3/2007 | Das et al. |
| 7,491,725 B2 | 2/2009 | Lajeunesse et al. |
| 7,622,473 B2 | 11/2009 | Arora et al. |
| 7,888,361 B2 | 2/2011 | Cai et al. |
| 8,338,425 B2 | 12/2012 | Tung |
| 8,563,554 B2 | 10/2013 | Liu et al. |
| 9,169,244 B2 | 10/2015 | Cai et al. |
| 9,382,219 B2 | 7/2016 | Das et al. |
| 2004/0054186 A1 | 3/2004 | Das et al. |
| 2004/0209930 A1 | 10/2004 | Carboni et al. |
| 2006/0211705 A1 | 9/2006 | Arora et al. |
| 2009/0076025 A1 | 3/2009 | Czarnik |
| 2009/0149399 A1 | 6/2009 | Tung |
| 2012/0087915 A1 | 4/2012 | Buggy et al. |
| 2014/0128410 A1 | 5/2014 | Cai et al. |
| 2015/0158830 A1 | 6/2015 | Das et al. |
| 2015/0166601 A1 | 6/2015 | Morgan et al. |
| 2016/0009732 A1 | 1/2016 | Harbeson |
| 2016/0264537 A1 | 9/2016 | Das et al. |
| 2017/0224680 A2 | 8/2017 | Laberge et al. |
| 2017/0224688 A1 | 8/2017 | Krejsa |

FOREIGN PATENT DOCUMENTS

CN 104130250 A 5/2014
EP 2535339 A1 12/2012

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
PubChem Structure search, performed on Apr. 2, 2018.*
International Search Authority Invitation to pay Additional Fees Unity of Invention Feb. 23, 2018.
International Search Report dated Apr. 25, 2018
This application is related to co-pending U.S. Appl. No. 15/839,469 entitled "Protein Kinase Inhibitors," filed on Dec. 12, 2017, and U.S. Appl. No. 15/939,534 entitled "Protein Kinase Inhibitors," filed on Dec. 12, 2017.
Guignabert C, et al. "Dasatinib Induces Lung Vascular Toxicity and Predisposes to Pulmonary hypertension" Journal of Clinical Investigation Sep. 2016, vol. 126, No. 9, pp. 3207-3218.
Tatarczuch M, et al. "Dasatinib Therapy can Result in Significant pulmonary Toxicity" American Journal of Hematology Dec. 2015, vol. 90, No. 12, pp. E224-E225.
Hartkamp LM, et al. "Bruton's Tyrosine Kinase in Chronic Inflammation: from Pathophysiology to Therapy" International journal of Interferon, Cytokine and Mediator Research Sep. 2015, vol. 7, pp. 27-34.
Gross S, et al. "Targeting Cancer with Kinase Inhibitors" Journal of Clinical Investigation May 2015, vol. 125, No. 5, pp. 1780-1789.
Yago MR et al., "The use of Betaine HCl to Enhance Dasatinib Absorption in Healthy Volunteers with Rabeprazole-Induced hypchlorhydria" The AAPS Journal Nov. 2014, vol. 16, No. 6, pp. 1358-1365.
Hendriks RW, et al. "Targeting Bruton's Tyrosine Kinase in B Cell Malignancies" Nature Reviews Cancer 2014, vol. 14, pp. 219-232.
Timmins GS et al., "Deuterated Drugs; Where Are We Now?" Expert Opin Ther Pat. Oct. 2014, vol. 24, No. 10, pp. 1067-1075.
Wang X, et al. "Differential Effects of Dosing Regimen on the Safety and Efficacy of Dasatinib: Retrospective Exposure-Response Analysis of a Phase III Study" Clinical Pharmacology: Advances and Applications Jun. 2013, vol. 5, pp. 85-97.

(Continued)

Primary Examiner — Jeffrey H Murray
(74) Attorney, Agent, or Firm — Wuersch & Gering LLP; Maria Luisa Palmese; Thomas F. Woolf

(57) ABSTRACT

The present invention is directed to novel protein kinase inhibitors comprising the chemical compound N-(2-chloro-6-methylphenyl)-2-[[2-methyl-6-(3-hydroxypyrrolidin-1-yl)pyrimidin-4-yl]amino]thiazole-5-carboxamide, its pharmaceutically acceptable salts, enantiomers, and enantiomeric mixtures, and methods of use to treat protein kinase-mediated diseases or conditions.

12 Claims, 5 Drawing Sheets

(56) References Cited

OTHER PUBLICATIONS

Liu F, et al. "Synthesis and Biopharmaceutical Studies of JLTN as Potential Dasatinib Prodrug" Chem. Pharm. Bull. 2013, vol. 61, No. 8, pp. 877-881.

Takahashi N, et al. "Pharmacokinetics of Dasatinib for Philadelphia-Positive Acute Lymphocytic Leukemia with Acquired T3151 Mutation" Journal of Hematology & Oncology 2012, vol. 5: 23.

Secord AA, et al. "A Phase I Trial of Dasatinib, an Src-Family Kinase Inhibitor, in Combination with Paclitaxel and Carboplatin in Patients with Advanced or Recurrent Ovarian Cancer" Clin Cancer Res 2012, vol. 18, No. 19, p. 5489-5498.

Reardon DA, et al. "Phase 1 Trial of Dasatinib Plus Erlotinib in Adults with Recurrent Malignant Glioma" J Neurooncology 2012, vol. 108, No. 3, pp. 499-506.

Takahashi S, et al. "Phase I Study of Dasatinib (BMS-354825) in Japanese Patients with Solid Tumors" Cancer Science 2011, vol. 102, pp. 2058-2064.

Sen B, et al. "Regulation of SRC Family Kinases in Human Cancer" Journal of Signal Transduction 2011, Article ID 865819.

Mayer EL, et al. "A Phase 2 Trial of Dasatinib in Patients with Advanced HER2-Positive and/or Hormone receptor-Positive Breast Cancer" Clin Cancer Res 2011, vo. 17, No. 21, pp. 6897-6904.

Brooks HD, et al. "Phase II Study of Dasatinib in the Treatment of Head and Neck Squamous Cell Carcinoma (HNSCC)" Cancer 2011, vol. 117, No. 10, pp. 2112-2119.

Argiris A, et al. Phase I and Pharmacokinetic Study of Dasatinib and Cetuximab in Patients with Advanced Solid Malignancies Invest new Drugs 2012, vol. 30, No. 4, pp. 1575-1584.

Apenc R, et al. "Pediatric Phase I Trial and Pharmacokinetic Study of Dasatinib: A report From the Children's Oncology Group Phase I Consortium" Journal of Clinical Oncology 2011, vol. 29, No. 7, pp. 839-844.

Amrein PC, et al. "Phase II Study of Dasatinib in Relapsed or Refractory Chronic Lymphocytic Leukemia" Clin Cancel Res 2011, vol. 17, No. 9, pp. 2977-2986.

Johnson FM, et al. "Phase 1 Pharmacokinetic and Drug-Interaction Study of Dastinib in Patients With Advanced Solid Tumors" Cancer 2010, vol. 116, pp. 1582-1591.

Haura EB, et al. "Phase I/II Study of the Src Inhibitor Dasatinib in Combination With Erlotinib in Advanced Non-Small-Cell Lung Cancer" Journal of Clinical Oncology 2010, vol. 28, No. 8, pp. 1387-1394.

Snead JL, et al. "Acute Dasatinib Exposure Commits Bcr-Abl-Dependent Cells to Apotptosis" Blood 2009, vol. 114, No. 16, pp. 3459-3463.

Lagas JS, et al. "Brain Accumulation of Dasatinib Is Restricted by P-Glycoprotein (ABCB1) and Breast cancer Resistance Protein (ABCG2) and Can Be Enhanced by Elacridar Treatment" Clin Cancer Res 2009, vol. 15, No. 7, pp. 2344-2351.

Demetri GD, et al. "Phase I Dose-Escalation and Pharmacokinetic Study of Dasatinib in Patients with Advanced Solid Tumors" Clin Cancer Res 2009, vol, 16, No. 19, pp. 6232-6240.

Chen Y, et al. "P-Glycoprotein and Breast Cancer Resistance protein influence Brain Distribution of Dasatinib" Journal of Pharmacology and Experimental Therapeutics 2009, vol. 330, No. 3, pp. 956-963.

Li W, et al. "Metabolite Generation via Microbial Biotransformations with Actinomycetes: Rapid Screening for Active Strains and Biosynthesis of Important Human Metabolites of Two Development-Stage Compounds, 5-[(5S,9R)-9-(4-Cyanophenyl)-3-(3,5-dichlorophenyl)-1-methyl-2,4-dioxo-1,3,7-triazaspiro[4.4]non7-yl-methyl]-3-thiophenecarboxylic Acid (BMS-587101) and Dasatinib" Drug Metabolism and Disposition 2008, vol. 36, No. 4, pp. 721-730.

Hiwase DK, et al. "Dasatinib Cellular Uptake and Efflux in Chronic Myeloid Leukemia Cells: Therapeutic Implications" Clin Cancer Res 2008, vol. 14, No. 12, pp. 3881-3888.

He K, et al. "Lacteal Secretion, Fetal and Maternal Tissue Distribution of Dasatinib in Rats" Drug Metabolism and Disposition 2008, vol. 36, No. 12, pp. 2564-2570.

Christopher LJ, et al. "Metabolism and Disposition of Dasatinib After Oral Administration to Humans" Drug Metabolism and Disposition 2008, vol. 36, No. 7, pp. 1357-1364.

Christopher LJ, et al. "Biotransformation of [14C]Dasatinib: In Vitro Studies in rat, monkey, and Human and Disposition after Administration to Rats and Monkeys" Drug Metabolism and Disposition 2008, vol. 36, No. 7, pp. 1341-1356.

Quintas-Cardama A, et al. "Pleural Effusion in Patients With Chronic Myelogenous leukemia Treated With Dasatinib After Imatinib Failure" Journal of Clinical Oncology 2007, vol. 25, No. 25, pp. 3908-3914.

Luo FR, et al. "Dasatinib (BMS-354825) Pharmacokinetics and Pharmacodynamic Biomarkers in Animal Models Predict Optimal Clinical Exposure" Clin Cancer Res 2006, vol. 12, No. 23, pp. 7180-7186.

Das J, et al. "2-Aminothiazole as a Novel Kinase Inhibitor Template. Structure-Activity Relationship Studies toward the Discovery of N-(2-Chloro-6-methylphenyl)-2-[[6-[4-(2-hydroxyethyl)-1-piperazinyl}]-2-methyl-4-pyrimidinyl]amino)]-1,3-thiazole-5-carboxamide (Dasatinib, BMS-354825) as a Potent pan-Src Kinase Inhibitor" Journal of Medicinal Chemistry 2006, vol. 49, pp. 6819-6832.

Lombardo LJ, et al. "Discovery of N-(2-Chloro-6-methyl-phenyl)-2-(6-(4-(2-hydroxyethyl)-piperazine-1-yl)-2-methylpyrimidin-4-ylamino)thiazole-5-carboxamide (BMS-354825), a Dual Src/Abl Kinase Inhibitor with Potent Antitumor Activity in Preclinical Assays" Journal of Medicinal Chemistry 2004, vol. 47, pp. 6658-6661.

Kamath AV, et al. "Preclinical pharmacokinetics and in vitro metabolism of dasatinib (BMS-354825): a potent oral multi-targeted kinase inhibitor against SRC and BCR-ABL" Cancer Chemother. Pharmacol. 2008, vol. 61, pp. 365-376.

Iurlo A, et al. "Pleural effusion and molecular response in dasatinib-treated chronic myeloid leukemia patients in a real-ife Italian multicenter series" Ann. Hematol. Oct. 2, 2017 (published online), DOI 10.1007/s00277-017-3144-1, pp. 1-6.

* cited by examiner

PROTEIN KINASE INHIBITORS

CROSS REFERENCE TO RELATED APPLICATIONS

This application claims the benefit to U.S. Provisional Application No. 62/539,785 filed on Aug. 1, 2017 and to U.S. Provisional Application No. 62/433,410 filed on Dec. 13, 2016, the entire contents of which are incorporated herein by reference.

FIELD OF THE INVENTION

The present invention relates to novel deuterated and non-deuterated cyclic chemical compounds and salts thereof, to methods of using such compounds in treating protein kinase-mediated diseases or conditions such as autoimmune and cancer diseases or conditions, to pharmaceutical compositions of said compounds, and to combination treatments of said compounds with co-administered therapeutic agents.

BACKGROUND OF THE INVENTION

The information provided herein is intended solely to assist the understanding of the reader. None of the information provided nor references cited is admitted to be prior art to the present invention.

The identification of the molecular events that underlie the development of human diseases presents a major challenge in the design of improved strategies in the prevention, management, and cure of certain diseases (Lahiry P et al. Kinase mutations in human disease: interpreting genotype-phenotype relationships. Nat Rev Genet. 2010; 11(1):60-74).

The role of aberrantly regulated protein tyrosine kinases (PTKs) in human diseases is the subject of intense investigation (Lahiry id.). Protein kinases are regulators of cellular signaling, and their functional dysregulation is common in carcinogenesis, autoimmune reactions, and many other disease states or conditions (Lahiry id.; Vargas L et al. Inhibitors of BTK and ITK: state of the new drugs for cancer, autoimmunity and inflammatory diseases. Scand J Immunol. 2013; 78(2):130-9; Nobel M E et al. Protein kinase inhibitors: insights into drug design from structure. Science. 2004; 303:1800-1805). The human genome encodes over 500 protein kinases that share a catalytic domain conserved in sequence and structure but which are notably different in how their catalysis is regulated (Manning G et al. The protein kinase complement of the human genome. Science. 2002; 298:1912-1934; Nobel id.). Protein kinases regulate key signal transduction cascades that control or are involved in the control of physiological functions, including cellular growth and proliferation, cell differentiation, cellular development, cell division, stress response, transcription regulation, aberrant mitogenesis, angiogenesis, abnormal endothelial cell-cell or cell-matrix interactions during vascular development, inflammation, Jun-N-terminal kinase (JNK) signal transduction, and several other cellular processes (Manning id). Protein kinase inhibitors have been established as promising drugs that inhibit overactive protein kinases in cancer cells (Gross S et al. Targeting cancer with kinase inhibitors. J Clin Invest. 2015; 125(5):1780-1789; Vargas id).

A partial, non-limiting list of kinases includes: ABL, ACK, ARG, BLK, BMX, BRK, BTK, CSK, DDR1, DDR2, EGFR, EPHA1, FGR, FMS, FRK, FYN(isoform a), FYN (isoform b), HCK, KIT, LCK, LYNa, PDGFRα, PDGFRβ, SRC, SRM, YES, PIK3CA/PIK3R1 (Manning id). Aberrant kinase activity has been observed in many disease states including benign and malignant proliferative conditions as well as diseases resulting from inappropriate activation of the immune and nervous systems.

The novel compounds of this invention inhibit the activity of one or more protein kinases and are expected to be useful in treating kinase-related diseases or conditions.

SUMMARY OF INVENTION

The present invention concerns novel deuterated and non-deuterated cyclic chemical compounds and salts thereof active on protein kinases in general, and in particular as inhibitors of protein kinases. Additionally, methods of treating mammals with protein kinase-mediated diseases or conditions by administering a therapeutically effective amount of the novel deuterated or non-deuterated cyclic chemical compound and/or salts thereof to such mammals in need thereof.

In one aspect, the present invention provides compounds having formula I:

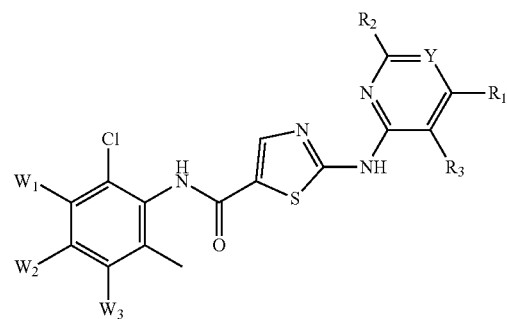

formula I all salts, prodrugs, enantiomers, and enantiomeric mixtures thereof;
wherein
$W_1$, $W_2$, and $W_3$ are independently hydrogen or deuterium;
Y is carbon or nitrogen;
$R_1$ is

-Q-A wherein
Q is a single bond directly attaching A to a ring carbon atom, or a methylene or ethylene group connecting A to a ring carbon atom; and
A is

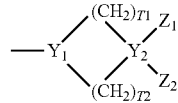

wherein
$Y_1$ and $Y_2$ are independently carbon or nitrogen;
$Z_1$ and $Z_2$ are independently hydrogen, —$(CH_2)_n$—$OR_5$ where n is an integer number from 0 to 4, and $R_5$ is hydrogen, lower alkyl, or lower alkenyl, with the proviso that when n is 1 and $R_5$ is hydrogen, $R_1$ is not a 1-piperidinyl group, and that when n is 2, $R_5$ is hydrogen, and $R_1$ is a 1-piperazinyl group, W$_2$ is deuterium, and —NR$_5$R$_6$ where R$_5$ and R$_6$ are independently hydrogen, lower alkyl, or lower alkenyl; T$_1$ and T$_2$ are independently an integer number from 0 to 4 with the proviso that when T$_1$ or T$_2$ is 0, —(CH$_2$)T$_1$ or —(CH$_2$)T$_2$ is a single bond, and T$_1$ and T$_2$ are not 0 at the same time;

R$_2$ and R$_3$ are independently hydrogen; halogen; alkoxyl; lower alkyl or lower alkenyl, wherein the lower alkyl or lower alkenyl is optionally substituted with one or more substituents selected from —OH and alkoxyl, wherein alkoxyl is methoxy, ethoxy, propyloxy, or tert-butoxy; or substituted heterocyclo including —NR$_5$R$_6$, wherein R$_5$ and R$_6$ are independently hydrogen, lower alkyl, or lower alkenyl;

and wherein the positions of R$_1$, R$_2$ and R$_3$ are exchangeable.

In one aspect, the present invention provides compounds having formula II:

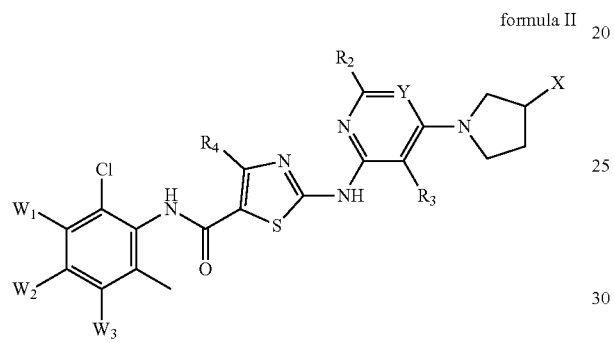

formula II all salts, prodrugs, enantiomers, and enantiomeric mixtures thereof:
wherein W$_1$, W$_2$, and W$_3$ are independently hydrogen or deuterium;
wherein Y is carbon or nitrogen;
wherein R$_2$, R$_5$, and R$_4$ are independently hydrogen; halogen; alkoxyl; lower alkyl or lower alkenyl, wherein the lower alkyl or lower alkenyl is optionally substituted with one or more substituents selected from —OH and alkoxyl, wherein alkoxyl is methoxy, ethoxy, propyloxy, or tert-butoxy; or substituted heterocyclo, wherein optionally substituted includes —NR$_5$R$_6$, wherein R$_5$ and R$_6$ are independently hydrogen, lower alkyl, or lower alkenyl; and
wherein X is independently hydrogen, —(CH$_2$)$_n$—OR$_5$ wherein n is an integer number from 0 to 4 and R$_5$ is hydrogen, lower alkyl, or lower alkenyl, or —NR$_5$R$_6$.

In one aspect, the present invention provides compounds having formula III:

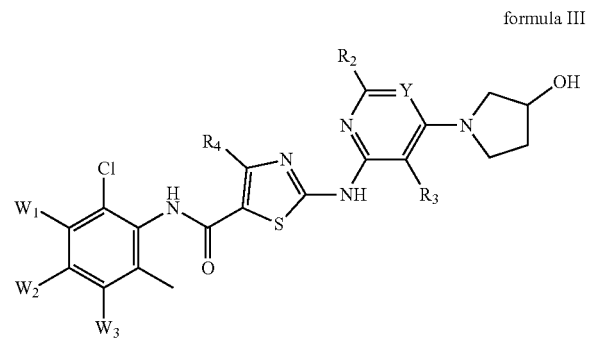

formula III all salts, prodrugs, enantiomers and enantiomeric mixtures thereof:
wherein W$_1$, W$_2$, and W$_3$ are independently hydrogen or deuterium;
wherein R$_2$, R$_3$, and R$_4$ are independently H; halogen; alkoxyl; lower alkyl or lower alkenyl, wherein the lower alkyl or lower alkenyl is optionally substituted with one or more substituents selected from —OH and alkoxyl, wherein alkoxyl is methoxy, ethoxy, propyloxy, or tert-butoxy; or substituted heterocyclo, wherein optionally substituted includes —NR$_5$R$_6$, wherein R$_5$ and R$_6$ are independently hydrogen, lower alkyl, or lower alkenyl.

In one aspect, the present invention provides compounds having formula IV:

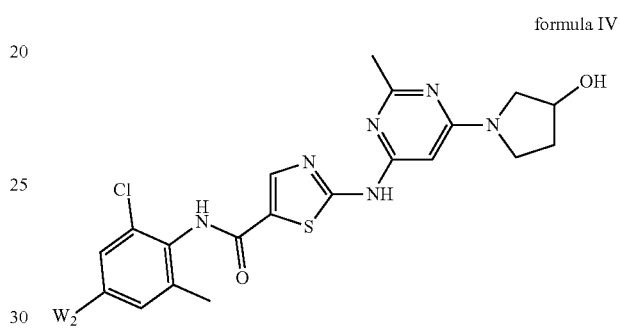

formula IV all salts, prodrugs, enantiomers and enantiomeric mixtures thereof:
wherein W$_2$ is hydrogen or deuterium.

In one aspect, the present invention provides compounds having formula V:

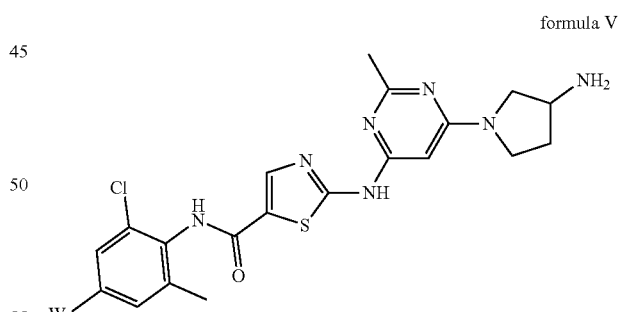

formula V all salts, prodrugs, enantiomers and enantiomeric mixtures thereof:
wherein W$_2$ is hydrogen or deuterium.

Exemplary compounds include the following deuterated and non-deuterated cyclic chemical compounds.

In one aspect, the present invention provides a compound having the structure of compound I:

compound I

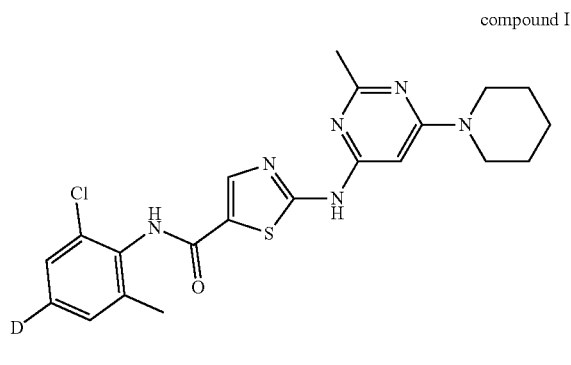 [SMILES: [2H]c1cc(C)c(NC(=O)c2cnc(Nc3cc(N4CCCCC4)nc(C)n3)s2)c(Cl)c1]

all salts and prodrugs thereof.

In one aspect, the present invention provides a compound having the structure of compound II:

compound II compound III

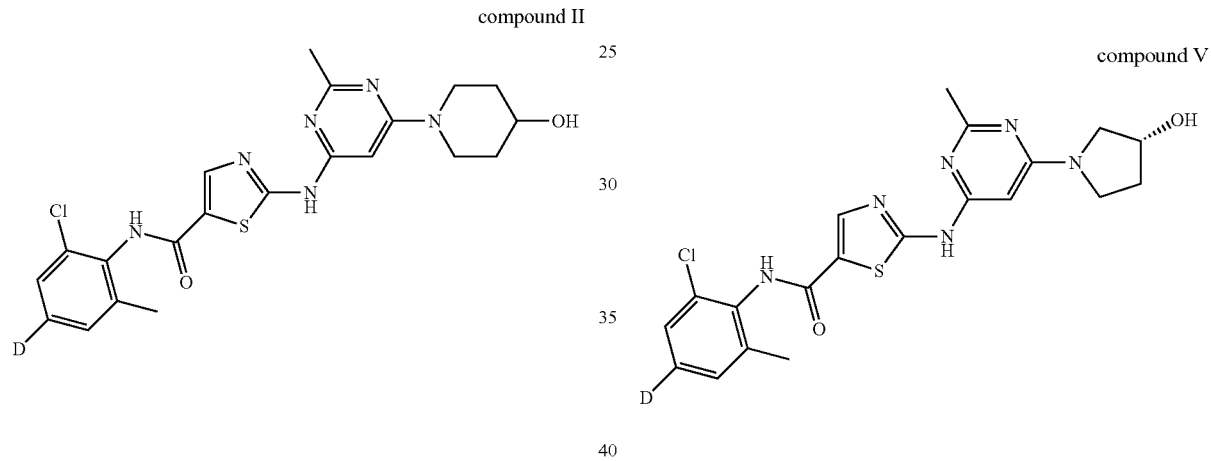

all salts and prodrugs thereof.

In one aspect, the present invention provides a compound having the structure of compound III:

all salts and prodrugs thereof.

In one aspect, the present invention provides a compound having the structure of compound IV:

compound IV compound V compound VI

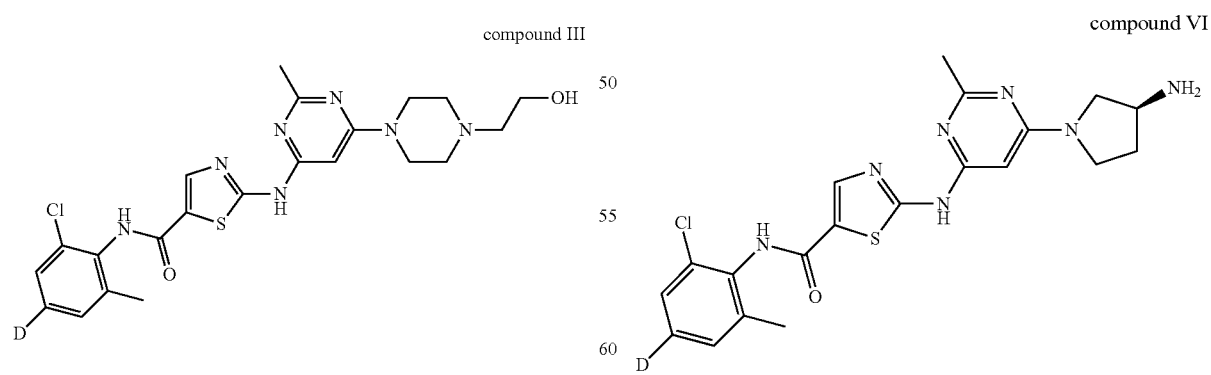

all salts and prodrugs thereof.

In one aspect, the present invention provides a compound having the structure of compound V:

all salts and prodrugs thereof.

In one aspect, the present invention provides a compound having the structure of compound VI:

all salts and prodrugs thereof.

In one aspect, the present invention provides a compound having the structure of compound VII:

compound VII

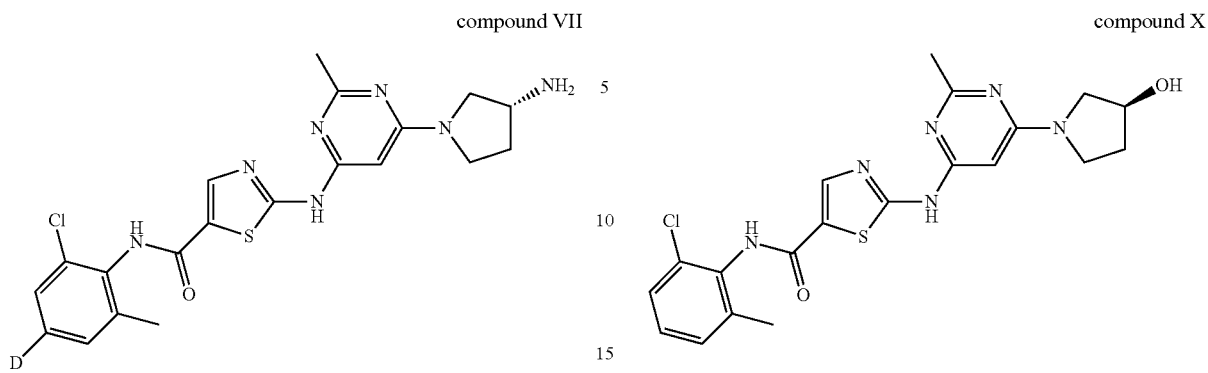

all salts and prodrugs thereof.

In one aspect, the present invention provides a compound having the structure of compound VIII:

compound VIII

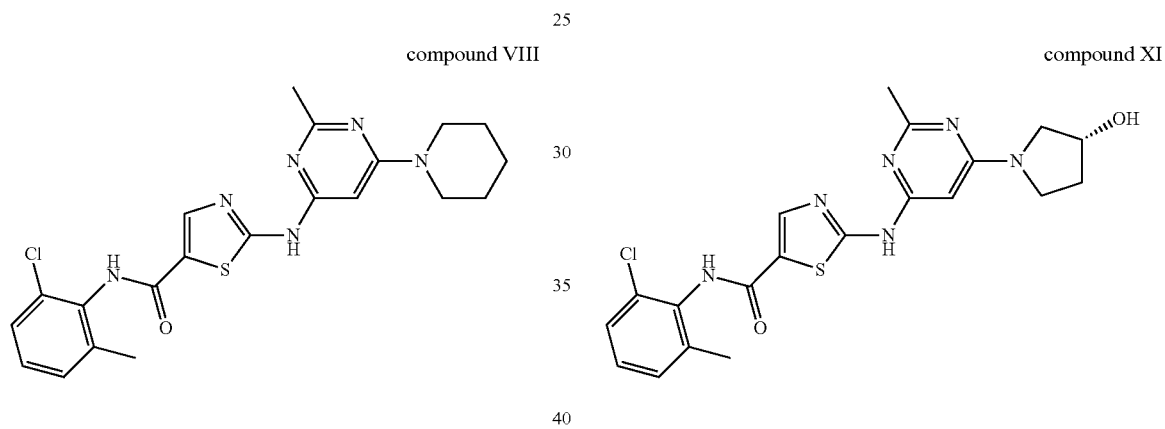

all salts and prodrugs thereof.

In one aspect, the present invention provides a compound having the structure of compound IX:

compound IX

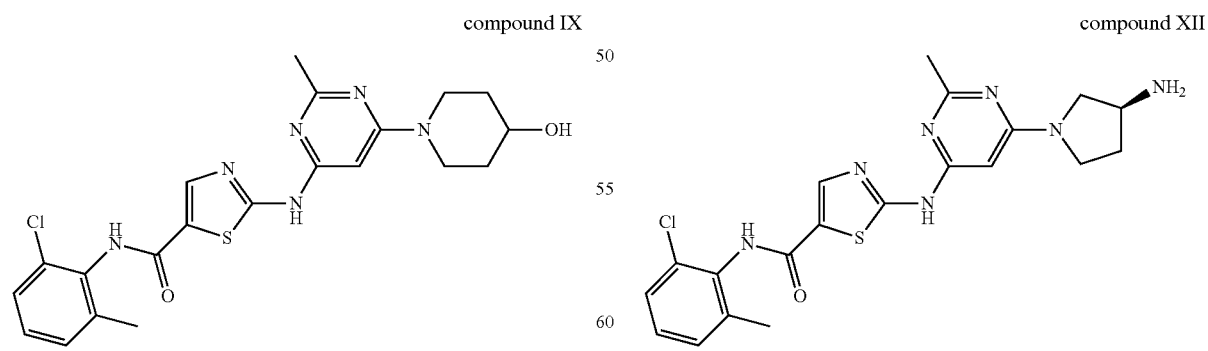

all salts and prodrugs thereof.

In one aspect, the present invention provides a compound having the structure of compound X:

compound X all salts and prodrugs thereof.

In one aspect, the present invention provides a compound having the structure of compound XI:

compound XI all salts and prodrugs thereof.

In one aspect, the present invention provides a compound having the structure of compound XII:

compound XII all salts and prodrugs thereof.

In one aspect, the present invention provides a compound having the structure of compound XIII:

compound XIII

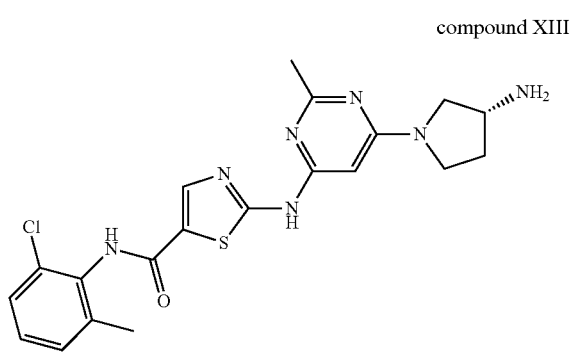 [SMILES: Cc1nc(Nc2ncc(C(=O)Nc3c(C)cccc3Cl)s2)cc(N2CC[C@@H](N)C2)n1]

all salts and prodrugs thereof.

In one aspect, the present invention provides a compound having the structure of compound XIV:

compound XIV

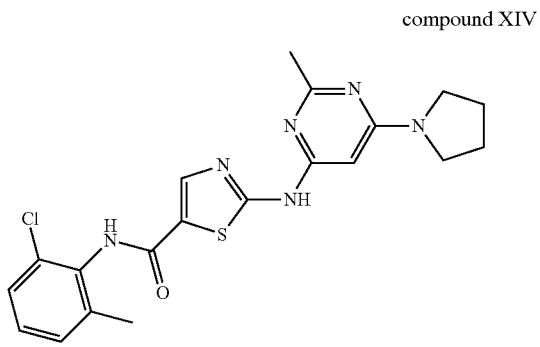 [SMILES: Cc1nc(Nc2ncc(C(=O)Nc3c(C)cccc3Cl)s2)cc(N2CCCC2)n1]

all salts and prodrugs thereof.

In one aspect, the invention provides a method for treating a protein kinase-mediated disease or condition in an animal or human subject wherein the method involves administering to the subject an effective amount of one or more of a compound selected from formulas I, II, III, IV, and/or V, and preferably one or more of compounds I, II, III, IV, V, VI, VII, VIII, IX, X, XI, XII, XIII, and/or XIV (compounds I-XIV), and more preferably compounds IV, V, X and/or XI.

The protein kinase mediated disease or condition is an autoimmune disease or a cancer. Preferably the autoimmune disease may be at least one of systemic lupus erythematosus (SLE), transplant rejection, multiple sclerosis (MS), systemic sclerosis (SSc), primary Sjögren's syndrome (pSS), rheumatoid arthritis (RA), and psoriasis. Preferably, the cancer is at least one of Philadelphia chromosome-positive (Ph+) chronic myeloid leukemia (CML), Philadelphia chromosome-positive acute lymphoblastic leukemia (Ph+ ALL), diffuse large B-cell lymphoma (DLBCL), chronic lymphocytic leukemia (CLL), follicular lymphoma, marginal zone lymphomas, mantle cell lymphoma (MCL), Waldenstrom's macroglobulinemia (WM), T-cell lymphomas, and multiple myeloma.

In one aspect, the invention provides a method of treating a subject suffering from a protein kinase-mediated disease or condition, comprising administering to the subject suffering from a protein kinase-mediated disease or condition in combination with at least one additional therapeutic agent one or more of a compound selected from formulas I, II, III, IV, and/or V, and preferably compounds I, II, III, IV, V, VI, VII, VIII, IX, X, XI, XII, XIII, and/or XIV (compounds I-XIV), and more preferably compounds IV, V, X and/or XI.

The terms "treat" or "therapy" and like terms refer to the administration of compounds in an amount effective to prevent, alleviate, or ameliorate one or more symptoms of a disease or condition, i.e., indication, and/or to prolong the survival of the subject being treated. The term "protein kinase-mediated disease or condition" refers to a disease or condition in which the biological function of a protein kinase affects the development, course, and/or symptoms of the disease or condition. A protein kinase-mediated disease or condition includes a disease or condition for which modulation of protein kinase activity provides a positive effect, i.e., one in which treatment with protein kinase inhibitors, including compounds described herein, provides a therapeutic benefit to the subject with or at risk of the disease or condition.

In one aspect, the invention provides for pharmaceutical compositions that include a therapeutically effective amount of one or more of a compound selected from formulas I, II, III, IV, and/or V, and preferably compounds I, II, II, IV, V, VI, VII, VIII, IX, X, XI, XII, XIII, and/or XIV (compounds I-XIV), and more preferably compounds IV, V, X, and/or XI in free form or in a pharmaceutically acceptable salt form and at least one pharmaceutically acceptable carrier, excipient, and/or diluent.

In reference to compounds of the invention a compound or group of compounds includes pharmaceutically acceptable salts of such compound(s) unless clearly indicated to the contrary, prodrug(s), and all stereoisomers and mixtures thereof.

DETAILED DESCRIPTION OF THE INVENTION

Definitions

Figure 1:
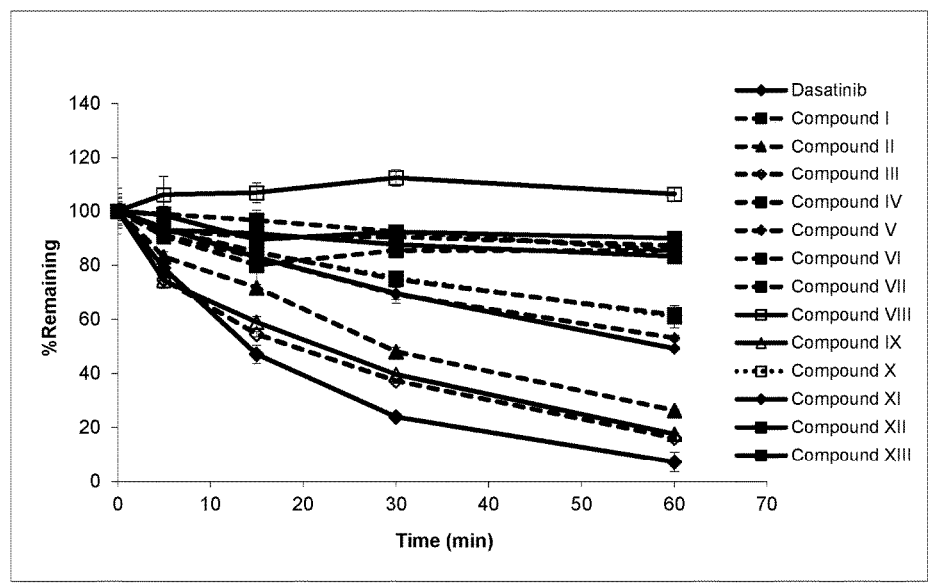
FIG. 1. Metabolic stability of compounds in human liver microsomal incubations. Metabolic stability was determined for compounds I-XIII in incubations with human liver microsomal preparations. Incubations of individual compounds I-XIII at 1 µM concentrations were carried out for up to 1 hour with human liver microsomes (0.5 mg/mL) in 0.1 M phosphate buffer containing 10 mM $MgCl_2$, 1 mM NADPH and 2 mM UDPGA at 37° C. Concentrations at specified times were determined by LC-MS/MS.

As used herein the following definitions apply unless clearly indicated otherwise. By "chemical structure" or "chemical substructure" is meant any definable atom or group of atoms that constitute an individually identifiable molecule, portion of a molecule, such as a substituent moiety, a core which is optionally substituted, and the like. Normally, chemical substructures of a ligand can have a role in binding of the ligand to a target molecule, or can influence the three-dimensional shape, electrostatic charge, and/or conformational properties of the ligand.

The term "prodrug" is a compound that, upon in vivo administration, is metabolized by one or more steps or processes or otherwise converted to the biologically, pharmaceutically, or therapeutically active form of the compound. To produce a prodrug, the pharmaceutically active compound is modified such that the active compound will be regenerated by metabolic or hydrolytic processes.

The term "binds," in connection with the interaction between a target and a potential binding compound, indicates that the potential binding compound associates with the target to a statistically significant degree as compared to association with proteins generally (i.e., non-specific binding).

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g., agonist, activator), or decreasing (e.g., antagonist, inhibitor) its activity. This type of activity is typically indicated in terms of an half maximal effective concentration ($EC_{50}$) or half maximal inhibitory concentration ($IC_{50}$) for an activator or inhibitor, respectively. Additionally, inhibition activity can be expressed in percent inhibition and/or Ki.

As used herein in connection with compounds of the invention, the term "synthesizing" and like terms means chemical synthesis from one or more precursor materials. Further, by "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

"D," "d," and "$^2$H" refer to a deuterium atom, a stable isotope of hydrogen with a mass twice that of hydrogen (atomic weight of 2.0144). Hydrogen naturally occurs as a mixture of the isotopes hydrogen ($^1$H), deuterium ($^2$H or D), and tritium ($^3$H or T). The natural abundance of deuterium is about 0.015%. A person skilled in the art would recognize that all chemical compounds with a hydrogen atom actually are present as mixtures of the H and D isotopes, with about 0.015% being the deuterium isotope. Compounds with a level of deuterium that has been enriched to be greater than its natural abundance of 0.015% should be considered unnatural, and as a result novel, over their non-enriched counterparts. The D in structural formulas and chemical compounds herein refers to incorporation of D in amounts greater than 0.015%.

The term "lower alkyl" is art-recognized, and includes saturated aliphatic groups, including straight-chain alkyl groups and branched-chain alkyl groups. In certain embodiments, a straight chain or branched chain alkyl has about 6 or fewer carbon atoms in its backbone (e.g., $C_1$-$C_6$ for straight chain, $C_3$-$C_6$ for branched chain).

The term "lower alkenyl" refers to an unsaturated straight or branched hydrocarbon having at least one carbon-carbon double bond, such as straight or branched group of 2-6 carbon atoms, referred to herein as $C_2$-$C_6$ alkenyl.

The term "cycloalkyl" refers to a 3-7 membered moncyclic ring of aliphatic groups, including $C_5$-$C_7$, that is optionally substituted with alkyl, alkenyl, alkoxyl, optionally substituted amino, halogens, cyano (—CN), or nitro (—$NO_2$).

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy, and the like.

The terms "heterocyclo," "heterocyclic," or "heterocycle" refer to fully saturated or unsaturated, including non-aromatic (i.e., "heterocycloalkyl") and aromatic (i.e., "heteroaryl") cyclic groups having from 5 to 10 atoms with at least one heteroatom (e.g. oxygen ("O"), sulfur ("S"), or nitrogen ("N")) in at least one carbon atom-containing ring.

Each ring of the heterocyclic group may have 1, 2, 3, or 4 heteroatoms. The heteroatoms nitrogen and sulfur may optionally be oxidized and the nitrogen heteroatom may optionally be quaternized. Further, the heterocyclo may be optionally substituted with amino (—$NR_5R_6$), wherein $R_5$ and $R_6$ are independently hydrogen and/or lower alkyl, hydroxyl (—OH), alkoxyl, lower alkyl or lower alkenyl, wherein the lower alkyl or lower alkenyl may be optionally substituted with —OH or alkoxyl groups.

"Halogen" refers to chloro ("Cl"), fluoro ("F"), bromo ("Br"), or iodo ("I").

It is to be understood that the compounds provided herein may contain chiral centers. Such chiral centers may be of either the (R) or (S) configuration, or may be a mixture thereof. Thus, the compounds provided herein may be enantiomerically pure, or stereoisomeric or diastereomeric mixtures thereof, including racemic mixtures (about 50:50 ratio of enantiomers).

The term "pharmaceutically acceptable" means that the indicated material does not have properties that would cause a reasonably prudent medical practitioner to avoid administration of the material to a patient, taking into consideration the disease or condition to be treated and the respective route of administration. For example, it is commonly required that such a material be essentially sterile, e.g., for injectable.

The term "pharmaceutically acceptable salts" refers to salts that are non-toxic in the amounts and concentrations at which they are administered. The preparation of such salts can facilitate the pharmacological use by altering the physical characteristics of a compound without preventing it from exerting its physiological effect.

The term "pharmaceutically acceptable composition" refers to a pharmaceutically active compound and one or more pharmaceutically acceptable carriers, excipients, and/or diluents.

The term "therapeutically effective" or "effective amount" is an amount of a preparation that alone, or together with further doses, and/or in combination with other therapeutic agents produces the desired response. This may involve halting the progression of the disease or delaying the onset of or preventing the disease or condition from occurring, although it may also imply only slowing of the disease or condition temporarily.

The term "protein kinase-mediated disease or condition" refers to a disease or condition in which the biological function of a protein kinase affects the development, course, and/or symptoms of the disease or condition.

The term "mutants" refers to single or multiple amino acid changes in a protein as compared to the wild-type protein amino acid sequence.

Throughout the description and claims of this specification, the word "comprise" and variations of the word, such as "comprising" and "comprises," means "including but not limited to," and is not intended to exclude, for example, other additives, components, integers, or steps.

Compounds of the Invention

In one aspect, the present invention provides compounds having formula I:

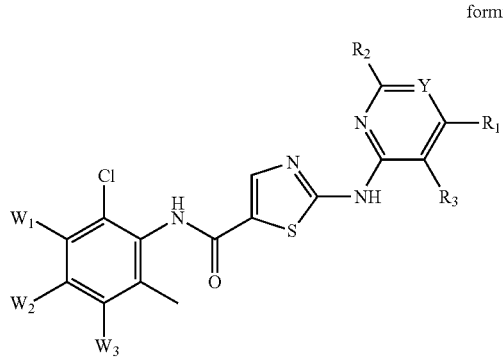

formula I all salts, prodrugs, enantiomers, and enantiomeric mixtures thereof;
wherein
$W_1$, $W_2$, and $W_3$ are independently hydrogen or deuterium;
Y is carbon or nitrogen;
$R_1$ is
  -Q-A
  wherein
  Q is a single bond directly attaching A to a ring carbon atom, or a methylene or ethylene group connecting A to a ring carbon atom; and
  A is

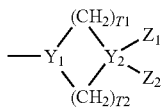

wherein
  $Y_1$ and $Y_2$ are independently carbon or nitrogen;
  $Z_1$ and $Z_2$ are independently hydrogen, —$(CH_2)_n$—$OR_5$ where n is an integer number from 0 to 4, and $R_5$ is hydrogen, lower alkyl, or lower alkenyl, with the proviso that when n is 1 and $R_5$ is hydrogen, $R_1$ is not a 1-piperidinyl group, and that when n is 2, $R_5$ is hydrogen, and $R_1$ is a 1-piperazinyl group, $W_2$ is deuterium, and —$NR_5R_6$ where $R_5$ and $R_6$ are independently hydrogen, lower alkyl, or lower alkenyl; $T_1$ and $T_2$ are independently an integer number from 0 to 4 with the proviso that when $T_1$ or $T_2$ is 0, —$(CH_2)T_1$ or —$(CH_2)T_2$ is a single bond, and $T_1$ and $T_2$ are not 0 at the same time;
$R_2$ and $R_3$ are independently hydrogen; halogen; alkoxyl; lower alkyl or lower alkenyl, wherein the lower alkyl or lower alkenyl is optionally substituted with one or more substituents selected from —OH and alkoxyl, wherein alkoxyl is methoxy, ethoxy, propyloxy, or tert-butoxy; or substituted heterocyclo including —$NR_5R_6$, wherein $R_5$ and $R_6$ are independently hydrogen, lower alkyl, or lower alkenyl;
and wherein the positions of $R_1$, $R_2$ and $R_3$ are exchangeable.

Preferably $W_2$ is deuterium or hydrogen, more preferably hydrogen, and $W_1$ and $W_3$ are hydrogen. Y is preferably nitrogen. $R_2$ is preferably lower alkyl, more preferably methyl. $R_3$ is preferably lower alkyl or hydrogen, more preferably hydrogen. $R_1$ is preferably a substituted or unsubstituted saturated five or six membered nitrogen containing heterocyclo ring. The substituted or unsubstituted saturated five membered nitrogen containing heterocyclo ring can be substituted or unsubstituted pyrrolidin-1-yl, preferably 3-hydroxy- or 3-amino-pyrrolidin-1-yl, more preferably 3-hydroxy pyrrolidin-1-yl.

In one aspect, the present invention provides compounds having formula II:

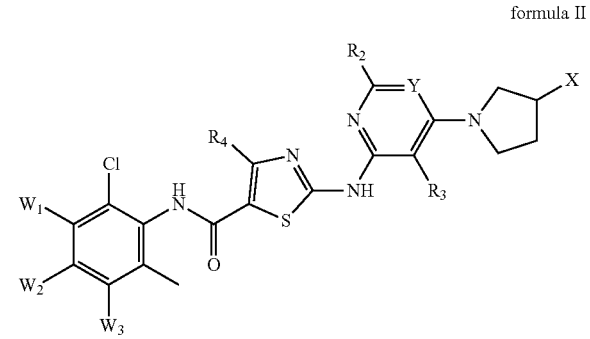

formula II all salts, prodrugs, enantiomers, and enantiomeric mixtures thereof:
wherein $W_1$, $W_2$, and $W_3$ are independently hydrogen or deuterium;
wherein Y is carbon or nitrogen;
wherein $R_2$, $R_3$, and $R_4$ are independently hydrogen; halogen; alkoxyl; lower alkyl or lower alkenyl, wherein the lower alkyl or lower alkenyl is optionally substituted with one or more substituents selected from —OH and alkoxyl, wherein alkoxyl is methoxy, ethoxy, propyloxy, or tert-butoxy; or substituted heterocyclo, wherein optionally substituted includes —$NR_5R_6$, wherein $R_5$ and $R_6$ are independently hydrogen, lower alkyl, or lower alkenyl; and
wherein X is independently hydrogen, —$(CH_2)_n$—$OR_5$ wherein n is an integer number from 0 to 4 and $R_5$ is hydrogen, lower alkyl, or lower alkenyl, or —$NR_5R_6$.
Preferably $W_2$ is deuterium or hydrogen, more preferably hydrogen, and $W_1$ and $W_3$ are hydrogen. Y is preferably nitrogen. $R_2$ is preferably lower alkyl, more preferably methyl. $R_3$ is preferably lower alkyl or hydrogen, more preferably hydrogen. Re is preferably lower alkyl or hydrogen, more preferably hydrogen. X is preferably hydrogen, hydroxyl or amine, more preferably hydroxyl.

In one aspect, the present invention provides compounds having formula III:

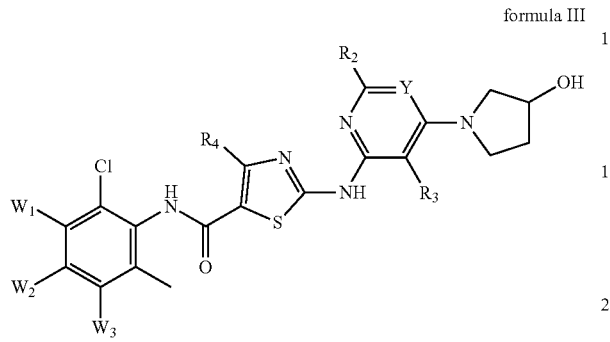

formula III all salts, prodrugs, enantiomers and enantiomeric mixtures thereof:
wherein $W_1$, $W_2$, and $W_3$ are independently hydrogen or deuterium;
wherein $R_2$, $R_3$, and $R_4$ are independently H; halogen; alkoxyl; lower alkyl or lower alkenyl, wherein the lower alkyl or lower alkenyl is optionally substituted with one or more substituents selected from —OH and alkoxyl, wherein alkoxyl is methoxy, ethoxy, propyloxy, or tert-butoxy; or substituted heterocyclo, wherein optionally substituted includes —$NR_5R_6$, wherein $R_5$ and $R_6$ are independently hydrogen, lower alkyl, or lower alkenyl.

Preferably $W_2$ is deuterium or hydrogen, more preferably hydrogen, and $W_1$ and $W_3$ are hydrogen. Y is preferably nitrogen. $R_2$ is preferably lower alkyl, more preferably methyl. $R_3$ is preferably lower alkyl or hydrogen, more preferably hydrogen. $R_4$ is preferably lower alkyl or hydrogen, more preferably hydrogen.

In one aspect, the present invention provides compounds having formula IV:

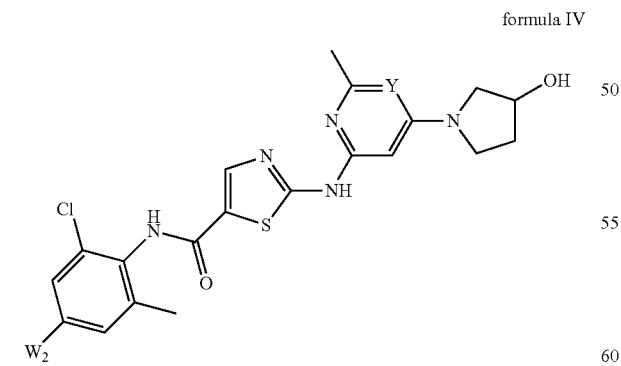

formula IV all salts, prodrugs, enantiomers and enantiomeric mixtures thereof:
wherein $W_2$ is hydrogen or deuterium.

In one aspect, the present invention provides compounds having formula V:

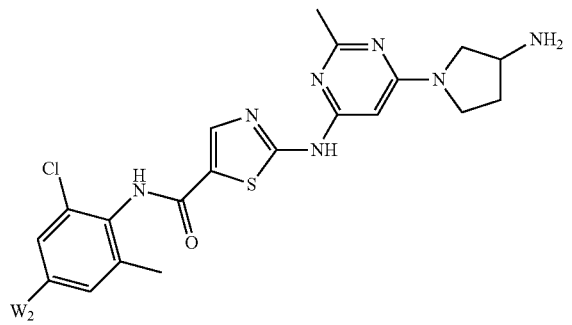

formula V all salts, prodrugs, enantiomers and enantiomeric mixtures thereof:
wherein $W_2$ is hydrogen or deuterium.

Exemplary Compounds

In one aspect, the present invention provides a compound having the structure of compound I:

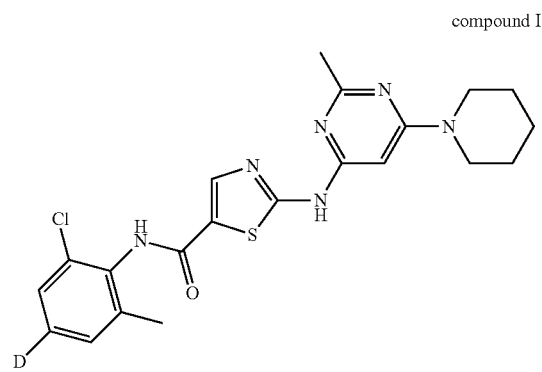 [SMILES: [2H]c1cc(C)c(NC(=O)c2cnc(Nc3cc(N4CCCCC4)nc(C)n3)s2)c(Cl)c1]

compound I all salts and prodrugs thereof.

In one aspect, the present invention provides a compound having the structure of compound II:

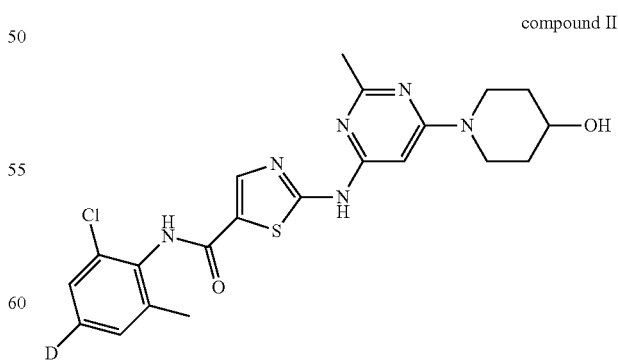

compound II all salts and prodrugs thereof.

In one aspect, the present invention provides a compound having the structure of compound III:

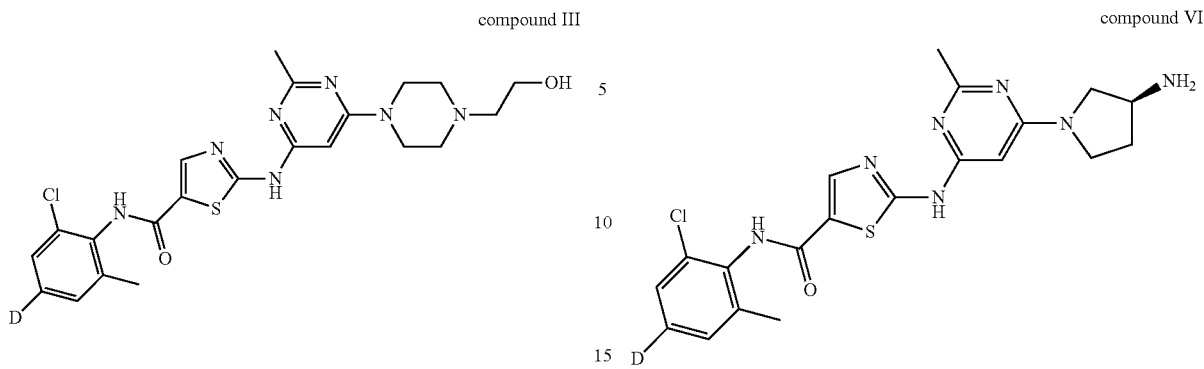

compound III all salts and prodrugs thereof.

In one aspect, the present invention provides a compound having the structure of compound IV:

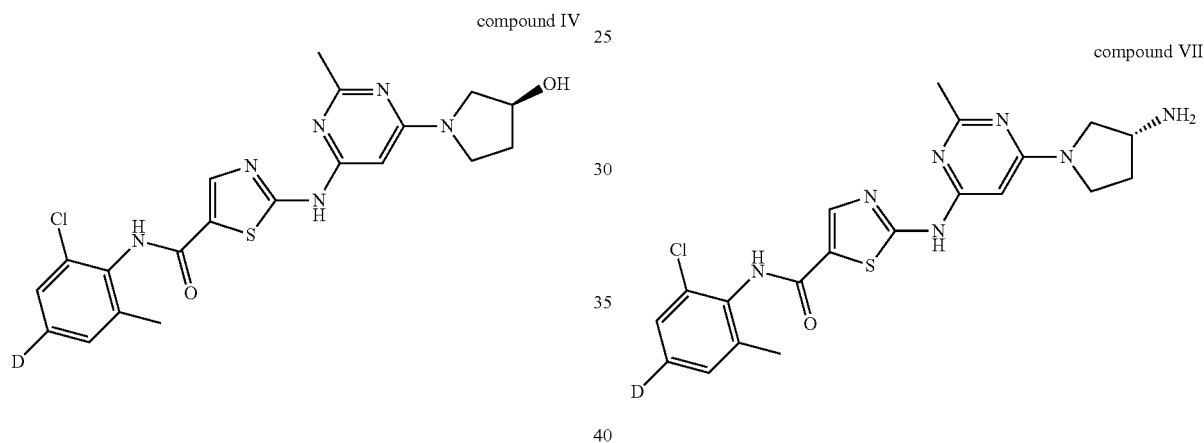

compound IV all salts and prodrugs thereof.

In one aspect, the present invention provides a compound having the structure of compound V:

compound V all salts and prodrugs thereof.

In one aspect, the present invention provides a compound having the structure of compound VI:

compound VI all salts and prodrugs thereof.

In one aspect, the present invention provides a compound having the structure of compound VII:

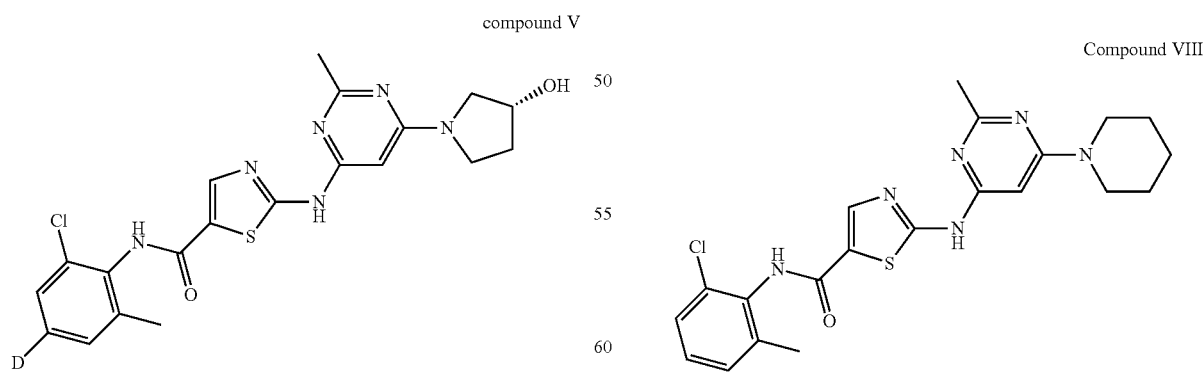

compound VII all salts and prodrugs thereof.

In one aspect, the present invention provides a compound having the structure of compound VIII:

Compound VIII all salts and prodrugs thereof.

In one aspect, the present invention provides a compound having the structure of compound IX:

Compound IX

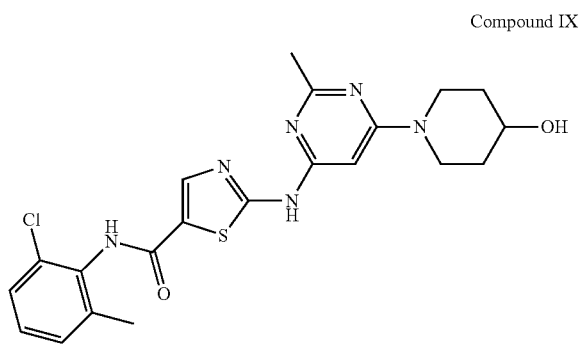 [SMILES: Cc1nc(Nc2ncc(C(=O)Nc3c(C)cccc3Cl)s2)cc(N2CCC(O)CC2)n1]

all salts and prodrugs thereof.

In one aspect, the present invention provides a compound having the structure of compound X:

compound X

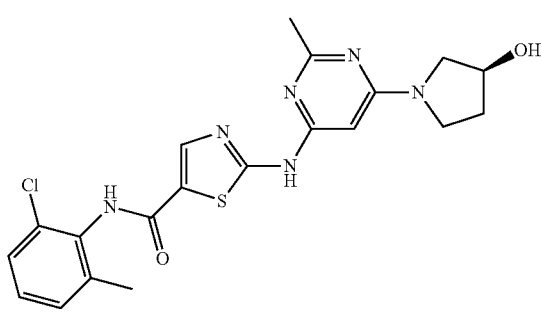

all salts and prodrugs thereof.

In one aspect, the present invention provides a compound having the structure of compound XI:

compound XI

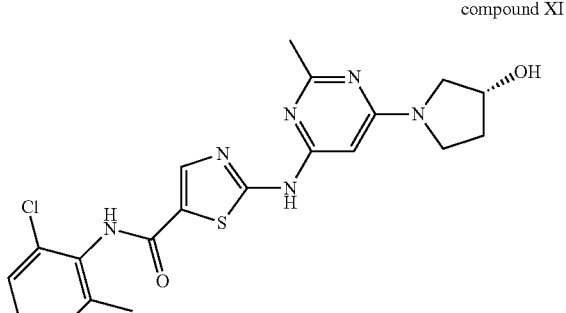

all salts and prodrugs thereof.

In one aspect, the present invention provides a compound having the structure of compound XII:

compound XII all salts and prodrugs thereof.

In one aspect, the present invention provides a compound having the structure of compound XIII:

compound XIII all salts and prodrugs thereof.

In one aspect, the present invention provides a compound having the structure of compound XIV:

compound XIV

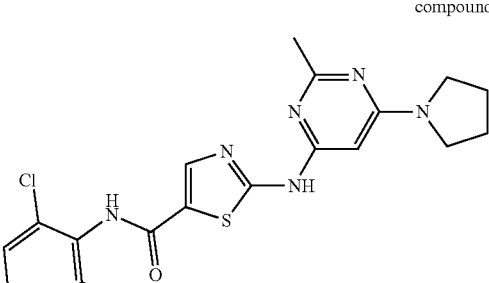

all salts and prodrugs thereof.

Protein Kinase Targets and Indications of the Invention

Protein kinases play key roles in propagating biochemical signals in diverse biological pathways. As such, kinases represent important control points for small molecule therapeutic intervention. More than 500 kinases have been described, and specific kinases have been implicated in a wide range of diseases or conditions. In one aspect, the invention provides methods for treating a protein kinase-mediated disease or condition in an animal or human subject, (i.e., indications), such as without limitation, autoimmune disease, hyperproliferative disease, cancer, cardiovascular disease, inflammatory disease, neurological disease, and other diseases.

Preferably, the protein kinase-mediated disease or condition is an autoimmune disease or cancer. More preferably, the autoimmune disease is at least one of systemic lupus erythematosus (SLE), transplant rejection, multiple sclerosis (MS), systemic sclerosis (SSc), primary Sjögren's syndrome (pSS), rheumatoid arthritis (RA), and psoriasis; and the cancer is at least one of Philadelphia chromosome-positive (Ph+) chronic myeloid leukemia (CML), Philadelphia chromosome-positive acute lymphoblastic leukemia (Ph+ ALL), diffuse large B-cell lymphoma (DLBCL), chronic lymphocytic leukemia (CLL), follicular lymphoma, marginal zone lymphomas, mantle cell lymphoma (MCL), Waldenstrom's macroglobulinemia (WM), T-cell lymphomas, and multiple myeloma.

In another aspect, the invention provides a method for modulating the activity of a protein kinase selected from the group consisting of ABL, ACK, ARG, BLK, BMX, BRK, BTK, CSK, DDR1, DDR2, EGFR, EPHA1, FGR, FMS, FRK, FYN, HCK, KIT, LCK, LYN, PDGFRα, PDGFRβ, SRC, SRM, YES, PIK3CA/PIK3R1 by administering an effective dose amount of one or more compounds having formulas I, II, III, IV, and/or V, preferably one or more of compounds I, II, III, IV, V, VI, VII, VIII, IX, X, XI, XII, XIII, and/or XIV (compounds I-XIV), and more preferably one or more of compounds IV, V, X, and/or XI. Upper and lower case for letters used in kinase nomenclature are used interchangeably in the present document.

In another aspect, the invention provides methods for treating a protein kinase-mediated disease or condition in an animal subject, wherein the method involves administering to the subject an effective amount of a composition including one or more compounds having formulas I, II, III, IV and/or V, preferably one or more of compounds I, II, III, IV, VI, V, VII, VIII, IX, X, XI, XII, XIII, and XIV (compounds I-XIV), and more preferably one or more of compounds IV, V, X, and XI.

In one aspect, the invention provides methods for treating a disease or condition mediated by a protein kinase selected from the group consisting of ABL, ACK, ARG, BLK, BMX, BRK, BTK, CSK, DDR1, DDR2, EGFR, EPHA1, FGR, FMS, FRK, FYN(isoform a), FYN(isoform b), HCK, KIT, LCK, LYNa, PDGFRα, PDGFRβ, SRC, SRM, YES, PIK3CA/PIK3R1 by administering an effective amount of one or more compounds having formulas I, II, III, IV, and/or V, preferably one or more of compounds I, II, III, IV, V, VI, VII, VIII, IX, X, XI, XII, XIII, and/or XIV (compounds I-XIV), and more preferably one or more of compounds IV, V, X, and/or XI.

A number of different assays for kinase activity can be utilized for testing to determine active modulators and/or determining specificity of a modulator for a particular kinase or group of kinases. In addition to the assay mentioned in the Examples below, the person of ordinary skill in the art will know and understand that other assays that can be utilized or can be modified for a particular application.

In a commonly used in vitro screen for measuring inhibition of a battery of selected protein kinases (see Example 15) including ABL, ABL(E255K), ACK, ARG, BLK, BMX, BRK, BTK, CSK, DDR1, DDR2, EGFR, EPHA1, FGR, FMS, FRK, FYN, HCK, KIT, LCK, LYN, PDGFRα, PDGFRβ, SRC, SRM, YES, and PIK3CA/PIK3R1, compounds I, II, III, IV, V, VI, VII, VIII, IX, X, XI, XII, and XIII were found to display potent activity to inhibit BTK, BMX, ABL, ABL(E255K), SRC, ACK, ARG, BLK, DDR2, EPHA, FGR, FMS, FRK, FYN, HCK, LCK, LYN, PDGFRα, PDGFRβ, YES, and PIK3CA/PIK3R1, among others.

In the above referenced in vitro screen of the battery of protein kinases (see Example 15), compounds I, II, III, IV, V, VI, VII, VIII, IX, X, XI, XII, and XIII displayed greater than 50% inhibition at 10 nM of BTK, BMX, ABL, ABL (E255K), SRC, ACK, ARG, BLK, DDR2, EPHA1, FGR, FMS, FRK, FYN(isoform a), HCK, LCK, LYNa, PDGFRα, PDGFRβ, YES, and PIK3CA/PIK3R1.

As a further test of biological activity, compounds of the invention were assayed for inhibition of cell growth using diffuse large B-cell lymphoma cell line SU-DHL-4 and chronic myelogenous leukemia cell line K-562 (see Example 16). In this cell-based assay, the $IC_{50}$ values for compounds I, II, III, IV, V, VI, VII, VIII, IX, X, XI, XII, XIII, and XIV were all less than 20 nM.

Protein kinase targets for compounds I, II, III, IV, V, VI, VII, VIII, IX, X, XI, XII, XIII, and XIV include, but are not limited to the following: ABL, ACK, ARG, BLK, BMX, BRK, BTK, CSK, DDR1, DDR2, EGFR, EPHA1, FGR, FMS, FRK, FYN, HCK, KIT, LCK, LYN, PDGFRα, PDGFRβ, SRC, SRM, YES, and PIK3CA/PIK3R1.

The Tec family of kinases forms the second largest class of cytoplasmic protein tyrosine kinases after the Src family kinases (SFKs) and consists of five mammalian members: Btk, Bmx (bone marrow kinase on the X-chromosome, also known as Etk), Itk (IL-2 inducible T-cell kinase), Rlk (resting lymphocyte kinase, also known as Txk), and Tec (Hartkamp et al. Bruton's tyrosine kinase in chronic inflammation: from pathophysiology to therapy. Int J Interferon Cytokine Mediat Res. 2015; 7: 27-34). Most of the Tec family of kinases are primarily expressed in the hematopoietic system, although both Tec and Bmx are also expressed in stromal tissues such as liver and endothelial cells, respectively. Activation of Tec family kinases upon cell-surface receptor triggering requires relocalization of the protein to the plasma membrane, which is mediated by the interaction of the PH domain with the lipid phosphatidylinositol (3,4,5) P3, formed by activated phosphatidylinositol-3 kinase. Subsequent phosphorylation by SFKs and autophosphorylation of tyrosine 223 result in the complete activation of Tec family of kinases.

BTK is the best-known member of the Tec family of kinases with BTK mutations leading to X-linked agammaglobulinemia in men and X-linked immunodeficiency in mice. BTK is a key regulator of B-cell development, activation, signaling, and survival (Hartkamp id). In addition, BTK plays an important role in a number of other hematopoietic cell-signaling pathways, e.g., toll-like receptor (TLR) and cytokine receptor-mediated TNF-alpha production in macrophages, IgE receptor (FcepsilonRI) signaling in mast cells, inhibition of Fas/APO-1 apoptotic signaling in B-lineage lymphoid cells, and collagen-stimulated platelet aggregation. BTK and other members of Tec family kinases can play a critical role in autoimmune diseases, such as systemic lupus erythematosus (SLE), multiple sclerosis (MS), type I diabetes (T1D), systemic sclerosis (SSc), primary Sjögren's syndrome (pSS), and rheumatoid arthritis (RA). The BTK inhibitor ibrutinib demonstrated high clinical activity in B-cell malignancies, especially in patients with chronic lymphocytic leukemia (CLL), mantle cell lymphoma (MCL), and Waldenstrom's macroglobulinemia (WM). However, resistance to ibrutinib has been demonstrated in a subgroup of patients receiving ibrutinib treatment, mainly due to the development of BTK mutant enzyme C481S (Woyach J A et al. Resistance mechanisms for the Bruton's tyrosine kinase inhibitor ibrutinib. N Engl J Med. 2014; 370(24):2286-94).

The tyrosine kinase BMX regulates inflammation induced by TNF and other mediators appear to do so by regulating the shared TAK1-TAB complex (Gottar-Guillier M et al. The tyrosine kinase BMX is an essential mediator of inflammatory arthritis in a kinase-independent manner. J Immunology. 2011; 186(10):6014). BMX kinase may play a role in the pathogenesis of glioblastoma, prostate, breast, and lung cancers. BMX has also shown potential as an antivascular therapy in combination with radiation or as a sensitizer to chemotherapeutic agents. (Jarboe J S et al. Mini-review: bmx kinase inhibitors for cancer therapy. Recent Pat Anticancer Drug Discov. 2013; 8(3):228-38).

Src family kinases (SFKs) consist of 11 nonreceptor tyrosine kinases, including Src, Fyn, Yes, Blk, Yrk, Frk (also known as Rak), Fgr, Hck, Lck, Srm, and Lyn (Sen B, Johnson F M. Regulation of SRC family kinases in human cancers. J Signal Transduct. 2011:ID865819). Src is found in keratinocytes, whereas Blk, Fgr, Hck, Lck, and Lyn are found primarily in hematopoietic cells. Frk occurs chiefly in bladder, breast, brain, colon, and lymphoid cells. Src family kinases are involved in proliferation and migration responses in many cell types.

Src is a non-receptor protein tyrosine kinase that plays a multitude of roles in cell signaling. Src is involved in the control of many functions, including cell adhesion, growth, movement, and differentiation. Src is widely expressed in many cell types, and can have different locations within a cell. Numerous human malignancies display increased SRC expression and activity, suggesting that SRC may be intimately involved in oncogenesis. SRC inhibitor bosutinib has been used or the treatment of Philadelphia chromosome-positive (Ph+) chronic myelogenous leukemia (CML), and saracatinib has been studied for potential treatment of Alzheimer's disease and schizophrenia.

ABL is a cytoplasmic and nuclear protein tyrosine kinase that has been implicated in processes of cell differentiation, cell division, cell adhesion, and stress response (Hantschel O. Structure, regulation, signaling, and targeting of abl kinases in cancer. Genes Cancer. 2012; 3:436-46). ABL mutations are associated with cancers such as chronic myeloid leukemia (CML), acute lymphoblastic leukemia (ALL), and acute myelogenous leukemia (AML). Several ABL inhibitors such as imatinib, dasatinib, and nilotinib have been used for treatment of CML, ALL, and AML. Dasatinib, a potent inhibitor of BCR-ABL is used for treatment of newly diagnosed Philadelphia chromosome-positive (Ph+) chronic myeloid leukemia (CML) in chronic phase, chronic, accelerated, or myeloid or lymphoid blast phase Ph+ CML with resistance or intolerance to prior therapy including imatinib, and Philadelphia chromosome-positive acute lymphoblastic leukemia (Ph+ ALL) with resistance or intolerance to prior therapy. However, dasatinib is associated with severe respiratory toxicity such as pleural effusion and pulmonary hypertension, which could be a result of dasatinib accumulation in lung tissue. (Quintás-Cardama A, et al. Pleural effusion in patients with chronic myelogenous leukemia treated with dasatinib after imatinib failure. J Clin Oncol. 2007; 25(25):3908-14; Guignabert C, et al. Dasatinib induces lung vascular toxicity and predisposes to pulmonary hypertension. J Clin Invest. 2016; 126(9):3207-18).

LCK is a 57.9 kDa membrane-associated non-receptor tyrosine kinase encoded by chromosome Ip34.3. The protein structure comprises an SH3 and SH2 domain. LCK inhibitors may be useful in treating acute lymphoblastic leukemia, T-cell lymphoma, lymphopenia, renal carcinoma, colon carcinoma, severe combined immunodeficiency, multiple sclerosis, inflammatory bowel, and type I diabetes.

Frk is a 58.5 kDa tyrosine kinase encoded by chromosome 6q21-q22.3. The structure comprises an SH2, an SH3, and a tyrosine kinase domain. Inhibition of Frk could provide means to suppress beta-cell destruction in type I diabetes. Frk inhibitors may be useful in treating acute myeloid leukemia and type I diabetes.

Fyn is a 60.6 kDa non-receptor tyrosine kinase encoded by chromosome 6q21. Fyn is involved in regulation of mast cell degranulation in a synergistic confluence of Fyn and Lyn pathways at the level of protein kinase C and calcium regulation. Fyn inhibitors may be useful in treating Alzheimer's disease, schizophrenia, and in prevention of metastases, e.g., in melanoma and squamous cell carcinoma.

HCK is a 59.5 kDa tyrosine kinase encoded by chromosome 20ql 1.21. The protein structure comprises an SH3, an SH2, and a bipartite kinase domain. HCK inhibitors may be useful in treating chronic myelogenous leukemia and acute lymphocytic leukemia.

Kit is a 109.9 kDa transmembrane tyrosine kinase encoded by chromosome 4ql2. Kit plays an important role in the development of melanocytes, mast, germ, and hematopoietic cells. Aberrant expression and/or activation of Kit has been implicated in a variety of pathologic states. Kit inhibitors may be useful in treating malignancies, including mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including asthma, rheumatoid arthritis, allergic rhinitis, multiple sclerosis, inflammatory bowel syndrome, transplant rejection, and hypereosinophilia.

LCK is a 57.9 kDa membrane associated non-receptor tyrosine kinase encoded by chromosome Ip34.3. The protein structure comprises an SH3 and SH2 domain. LCK inhibitors may be useful in treating acute lymphoblastic leukemia, T-cell lymphoma, lymphopenia, renal carcinoma, colon carcinoma, severe combined immunodeficiency, multiple sclerosis, inflammatory bowel, and type I diabetes.

Platelet-derived growth factor receptors (PDGF-R) are cell surface tyrosine kinase receptors for members of the platelet-derived growth factor (PDGF) family. PDGF subunits-A and -B are important factors regulating cell proliferation, cellular differentiation, cell growth and development, and many diseases including cancer. There are two forms of the PDGF-R, alpha and beta, each encoded by a different gene. PDGFRα is a 122.7 kDa transmembrane tyrosine kinase encoded by chromosome 4ql2 (symbol: PDGFRA). PDGFRβ is a 124.0 kDa transmembrane tyrosine kinase encoded by chromosome 5q31-q32 (symbol: PDGFRB). PDGFR inhibitors may be useful in treating various diseases such as idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis.

Yes is a 60.8 kDa tyrosine kinase encoded by chromosome 18pl 1.31-pl 1.21 (symbol: YESI). The structure of Yes comprises SH3 and SH2 domains followed by a TK domain. The YES oncogene is homologous to the Yamaguchi sarcoma virus gene, and the amino acid sequence of Yes shows a high degree of homology with that of the SRC gene product of Roussarcoma virus. The Yes kinase is highly expressed in multiple mammalian cell types, including neurons, spermatozoa, platelets, and epithelial cells. The target kinase Yes is amplified and overexpressed in various cancers including esophageal squamous cell carcinoma. Yes inhibitors may be useful in treating cancers including esophageal squamous cell carcinoma.

In one aspect, compounds of formulas I, II, III, IV, and V, preferably compounds I, II, III, IV, V, VI, VII, VIII, IX, X, XI, XII, XIII, and XIV (compounds I-XIV), including salts, prodrugs, and/or isomers thereof, can be used in preparation of medicaments for the treatment of a kinase-mediated disease or condition, in particular when the disease or condition is an autoimmune disease or cancer.

The amounts of compounds of formulas I, II, III, IV, and V, compounds I, II, III, IV, V, VI, VII, VIII, IX, X, XI, XII, XIII and XIV (compounds I-XIV), including salts, prodrugs, and/or isomers thereof, to be administered can be determined by standard procedures taking into account factors such as the compound's $IC_{50}$; the biological half-life of the compound; the age, size, and weight of the subject; and the condition associated with the subject. In general, routine experimentation in clinical trials will determine specific ranges for optimal therapeutic effect for each therapeutic agent and each administrative protocol and administration to specific patients will be adjusted to within effective and safe ranges depending on the patient's condition and responsiveness to initial administration. However, the ultimate administration protocol will be regulated according to the judgment of the attending clinician considering such factors as age, gender, condition, and size of the patient. Generally, doses of active compounds may range from about 0.01 mg/kg per day to about 1000 mg/kg per day. Compounds described herein can be administered in single or multiple doses.

Preclinical Pharmacokinetics

In Vitro Metabolic Stability:

An in vitro metabolic stability study in human liver microsomes was conducted for compounds I through XIII and dasatinib (see Example 17 for experimental conditions). Results from this study are shown in FIG. 1 and table 1.

Compounds I, IV, V, VI, VII, VIII, X, XI, XII and XIII displayed significantly greater stability as compared to dasatinib. The in vitro tin for compounds I, IV, V, VI, VII, VIII, X, XI, XII, and XIII were all >59 min compared to 16 min for dasatinib. This significant increase in metabolic stability for compounds I, IV, V, VI, VII, VIII, X, XI, XII, and XIII was unexpected. Longer in vitro metabolic stability half-life ($t_{1/2}$) is an indicator of longer in vivo human plasma $t_{1/2}$ for these compounds compared to dasatinb. Therefore, these compounds are expected to have a more favorable pharmacokinetic profile compared to dasatinib, specifically longer $t_{1/2}$, longer duration of action, less first pass effect, and higher oral bioavailability. The intrinsic clearances for compounds I, IV, V, VI, VII, VIII, X, XI, XII, and XIII were less than 24 μL/min/mg compared to 88 μL/min/mg for dasatinib.

Surprisingly compound III, a deuterium labeled analog of dasatinib, was found to have similar metabolic stability to dasatinib (FIG. 1, table 1). This was an unexpected finding given the reported in vitro metabolism of dasatinib in human liver microsomes where hydroxylation at the 4-position of the 2-chloro-6-methylphenyl ring is a route of oxidative metabolism (Christopher U et al. Biotransformation of [14C]dasatinib: in vitro studies in rat, monkey, and human and disposition after administration to rats and monkey. Drug Metab. Dispos. 2007; 36(7):1341-1356).

Compounds I, IV, V, VI, VII, VIII, X, XI, XII, and XIII, showed unexpectedly significantly increased metabolic stability in human liver microsomes compared to dasatinib, and deuterium substitution results in additional unexpected results as compared to dasatinib.

TABLE 1

In vitro $t_{1/2}$ and intrinsic clearance (CLint) of Compounds in human liver microsomal incubations*

|  | In vitro $t_{1/2}$ (min) | CLint (μL/min/mg) |
|---|---|---|
| Dasatinib | 16 | 88 |
| Compound I | 261 | 5 |
| Compound II | 32 | 44 |
| Compound III | 24 | 58 |
| Compound IV | 88 | 16 |
| Compound V | 67 | 21 |
| Compound VI | 403 | 3 |
| Compound VII | 404 | 3 |
| Compound VIII | >500 | <3 |
| Compound IX | 25 | 56 |
| Compound X | 87 | 16 |
| Compound XI | 59 | 24 |
| Compound XII | 448 | 3 |
| Compound XIII | 261 | 5 |

*Compound I-XIII (1 μM) were incubated with human liver microsomes (0.5 mg/mL) in 0.1M phosphate buffer containing 10 mM $MgCl_2$, 1 mM NADPH and 2 mM UDPGA at 37° C. for various time points through 60 min. The concentrations of remaining test compounds at the various time points were determined by LC-MS/MS.

Figure 2:
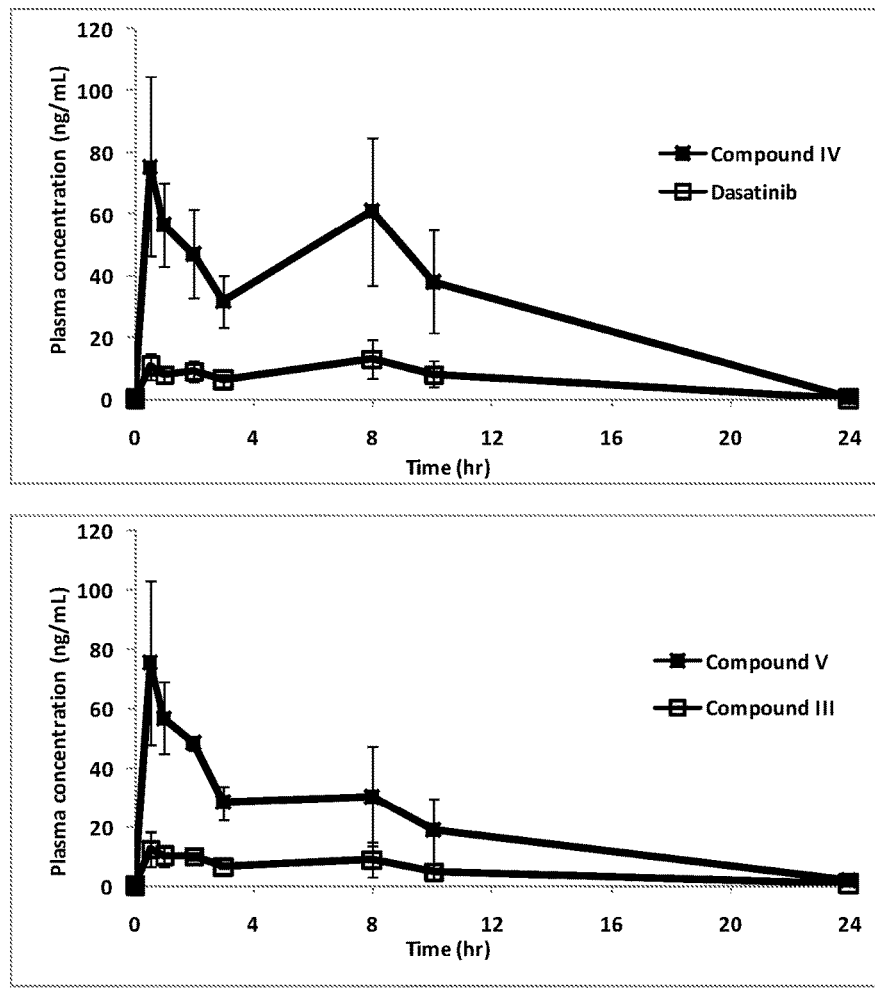
FIG. 2. (Upper panel) Plasma concentration versus time profiles for compound IV and dasatinib in Sprague-Dawley rats following a single oral gavage dose of compound IV and dasatinib administered together and each dosed at 2.5 mg/kg; (Lower panel) plasma concentration versus time profiles for compounds III and V in Sprague-Dawley rats following a single oral gavage dose of compounds III and V administered together and each dosed at 2.5 mg/kg together.
Figure 3:
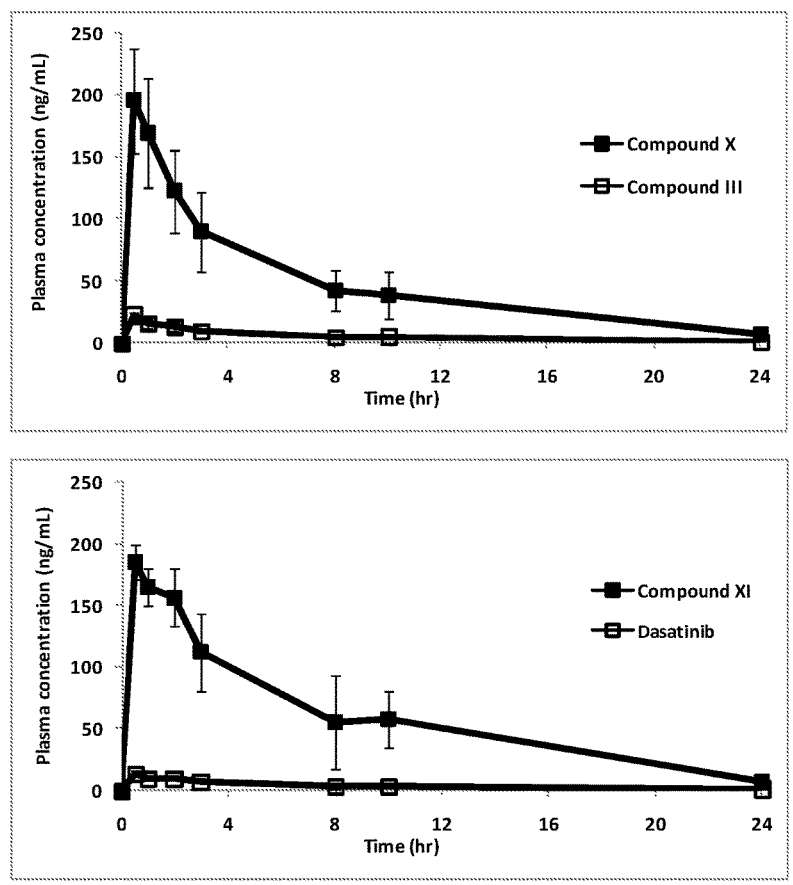
FIG. 3. (Upper panel) Plasma concentration versus time profiles for compounds X and III in Sprague-Dawley rats following a single oral gavage dose of compounds X and III administered together and each dosed at 5 mg/kg; (Lower panel) plasma concentration versus time profiles for compound XI and dasatinib in Sprague-Dawley rats following a single oral gavage dose of compound XI and dasatinib administered together and each dosed at 5 mg/kg together.

In Vivo Pharmacokinetics:

The in vivo pharmacokinetic profiles of compounds III, IV, V, X, XI, and dasatinib were investigated in Sprague Dawley rats following oral and intravenous administration using the technique of 2-in-1 dosing (see Example 18 for experimental conditions). Compound IV was dosed with dasatinib, compound V was dosed with compound III, compound X was dosed with dasatinib, and compound XI was dosed with compound III. Results are shown in FIGS. 2 and 3 and tables 2 and 3.

TABLE 2

Pharmacokinetic parameters of compounds III, IV, V and dasatinib in Sprague-Dawley rats following a single intravenous or oral dose administration (Example 18).

|  | Compound IV | | Dasatinib | | Compound V | | Compound III | |
|---|---|---|---|---|---|---|---|---|
|  | intravenous | PO | intravenous | PO | intravenous | PO | intravenous | PO |
| Dose (mg/kg) | 1 | 2.5 | 1 | 2.5 | 1 | 2.5 | 1 | 2.5 |
| $C_{max}$ (ng/mL) | N/A | 82 ± 23 | N/A | 15 ± 5 | N/A | 35 ± 19 | N/A | 9 ± 6 |
| $T_{max}$ (hr) | N/A | 5.5 ± 4.3 | N/A | 5.5 ± 4.3 | N/A | 5.5 ± 4.3 | N/A | 5.5 ± 4.3 |
| $AUC_{last}$ (ng/mL*hr) | 1877 ± 152 | 891 ± 341 | 783 ± 54 | 193 ± 86 | 1960 ± 214 | 524 ± 191 | 835 ± 114 | 139 ± 69 |

TABLE 2-continued

Pharmacokinetic parameters of compounds III, IV, V and dasatinib in Sprague-Dawley rats following a single intravenous or oral dose administration (Example 18).

| | Compound IV | | Dasatinib | | Compound V | | Compound III | |
|---|---|---|---|---|---|---|---|---|
| | intravenous | PO | intravenous | PO | intravenous | PO | intravenous | PO |
| $AUC_{inf}$ (ng/mL*hr) | 1879 ± 153 | 892 ± 341 | 784 ± 54 | 196 ± 85 | 1961 ± 214 | 539 ± 188 | 835 ± 114 | 144 ± 68 |
| $t_{1/2}$ (hr) | 1.4 ± 0.1 | 2.3 ± 0.2 | 1.5 ± 0 | 3.5 ± 0.5 | 1.4 ± 0.1 | 4.4 ± 2.8 | 1.6 ± 0.1 | 4.7 ± 2.2 |
| CL (mL/hr/kg) | 535 ± 45 | N/A | 1279 ± 88 | N/A | 514 ± 54 | N/A | 1211 ± 157 | N/A |
| V (L/kg) | 1 ± 0 | N/A | 3 ± 0 | N/A | 1 ± 0 | N/A | 3 ± 0 | N/A |
| F (%) | N/A | 18.9 ± 6.7 | N/A | 9.8 ± 3.6 | N/A | 11.1 ± 4.3 | N/A | 7.2 ± 4.2 |

Cmax—plasma maximum concentration following oral dosing; $T_{max}$—time to maximum plasma concentration following oral dosing; $AUC_{last}$—area under the plasma concentration versus time curve to the last detectable concentration; $AUC_{inf}$—area under the plasma concentration versus time curve extrapolated to time infinity; $t_{1/2}$—plasma concentration half-life; CL—plasma clearance; V—volume of distribution; F (%)—percent oral bioavailability as determined by $AUC_{inf}$(oral) versus $AUC_{inf}$(intravenous) dose normalized.

Additionally, compounds IV, V, X, and XI were found to have a surprisingly significantly lower intravenous volume of distribution values than dasatinib and compound III, suggesting these compounds are not as widely distributed to tissues as compared to dasatinib and compound III. Further, this suggests these compounds have lower potential than dasatinib for drug-induced organ toxicity.

These results indicate that chemical substitution on the pyrimidin-4-yl group to produce compounds IV, V, X, and

TABLE 3

Pharmacokinetic parameters of compounds III, X, XI, and dasatinib in Sprague-Dawley rats following a single intravenous or oral dose.

| | Compound X | | Dasatinib | | Compound XI | | Compound III | |
|---|---|---|---|---|---|---|---|---|
| | intravenous | PO | intravenous | PO | intravenous | PO | intravenous | PO |
| Dose (mg/kg) | 1 | 5 | 1 | 5 | 1 | 5 | 1 | 5 |
| $C_{max}$ (ng/mL) | N/A | 93 ± 101 | N/A | 7 ± 7 | N/A | 102 ± 86 | N/A | 11 ± 11 |
| $T_{max}$ (hr) | N/A | 0.5 ± 0 | N/A | 0.5 ± 0 | N/A | 0.5 ± 0 | N/A | 0.5 ± 0 |
| $AUC_{last}$ (ng/mL*hr) | 2519 ± 446 | 1122 ± 369 | 1013 ± 68 | 93 ± 23 | 2480 ± 243 | 1420 ± 343 | 916 ± 161 | 124 ± 26 |
| $AUC_{inf}$ (ng/mL*hr) | 2520 ± 446 | 1204 ± 349 | 1014 ± 68 | 97 ± 22 | 2481 ± 243 | 1495 ± 273 | 917 ± 161 | 137 ± 20 |
| t½ (hr) | 1.6 ± 0.2 | 6.8 ± 4.1 | 1.7 ± 0.3 | 5.9 ± 1.5 | 1.6 ± 0.2 | 6 ± 3.6 | 1.7 ± 0.2 | 8.2 ± 4.1 |
| CL (mL/hr/kg) | 405 ± 66 | N/A | 989 ± 64 | N/A | 406 ± 42 | N/A | 1113 ± 193 | N/A |
| V (L/kg) | 1 ± 0 | N/A | 2 ± 0 | N/A | 1 ± 0 | N/A | 3 ± 0 | N/A |
| F (%) | N/A | 18.9 ± 2.2 | N/A | 3.9 ± 1 | N/A | 24 ± 3.1 | N/A | 6 ± 0.9 |

Cmax—plasma maximum concentration following oral dosing; $T_{max}$—time to maximum plasma concentration following oral dosing; $AUC_{last}$—area under the plasma concentration versus time curve to the last detectable concentration; $AUC_{inf}$—area under the plasma concentration versus time curve extrapolated to time infinity; $t_{1/2}$—plasma concentration half-life; CL—plasma clearance; V—volume of distribution; F (%)—percent oral bioavailability as determined by $AUC_{inf}$(oral) versus $AUC_{inf}$(intravenous) dose normalized.

Following oral administrations, compounds IV, V, X, and XI showed surprisingly significantly higher Cmax values of 82±13, 35±19, 93±101, and 102±86 ng/mL, respectively, as compared to dasatinib where Cmax was 15±5 and 7±7 ng/mL and the deuterium analog of dasatinib, compound III, where Cmax was 9±6 and 11±11 ng/mL. The oral bioavailability of compounds IV, V, X, and XI was 18.9±6.7, 11.1±4.3, 18.9±2, and 24±33.1 percent bioavailability (F) compared to dasatinib oral bioavailability of 3.9±1 and 9.8±3.6 percent bioavailability, and compound III where oral bioavailability was 6±0.9 and 7.2±4.2 percent. The results from this study show compounds IV, V, X, and XI have surprisingly much lower intravenous plasma clearance than dasatinib and compound III. This data is consistent with the in vitro metabolic stability data which showed compounds IV, V, X, and XI to be significantly more stable than either dasatinib or compound III, and with significantly lower intrinsic clearance values.

XI results in unexpected and significant changes in the pharmacokinetic profile of these novel compounds as compared to dasatinib.

In Vivo Tissue Distribution: A study was conducted in mice to determine the ratio of parent compound concentrations in lung tissue versus plasma for compounds X, XI, and dasatinib dosed by oral gavage (see Example 19 for experimental conditions). Results are shown in FIGS. 4 and 5.

Figure 4:
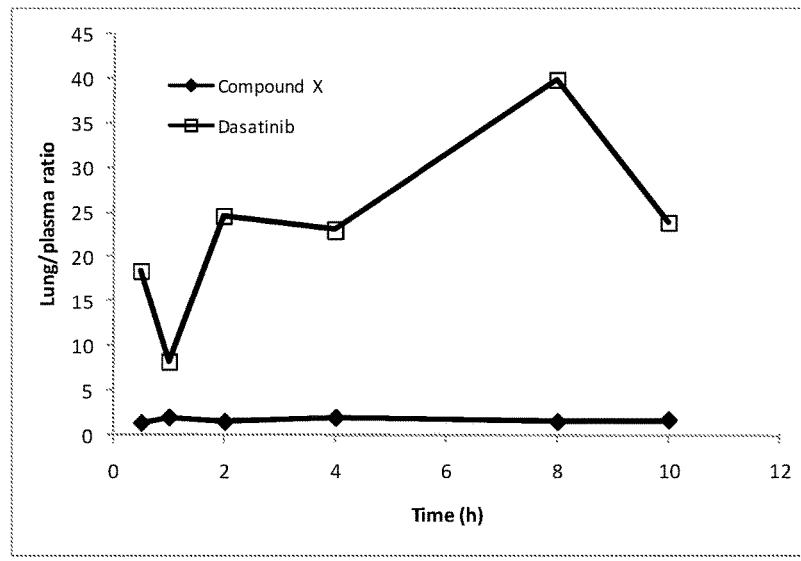
FIG. 4. Mean ratios of lung tissue concentration to plasma concentration versus time for compound X and dasatinib in mice wherein compound X and dasatinib were administered together as a single oral dose and each dosed at 5 mg/kg. (2-in-1 dosing, N=3).
Figure 5:
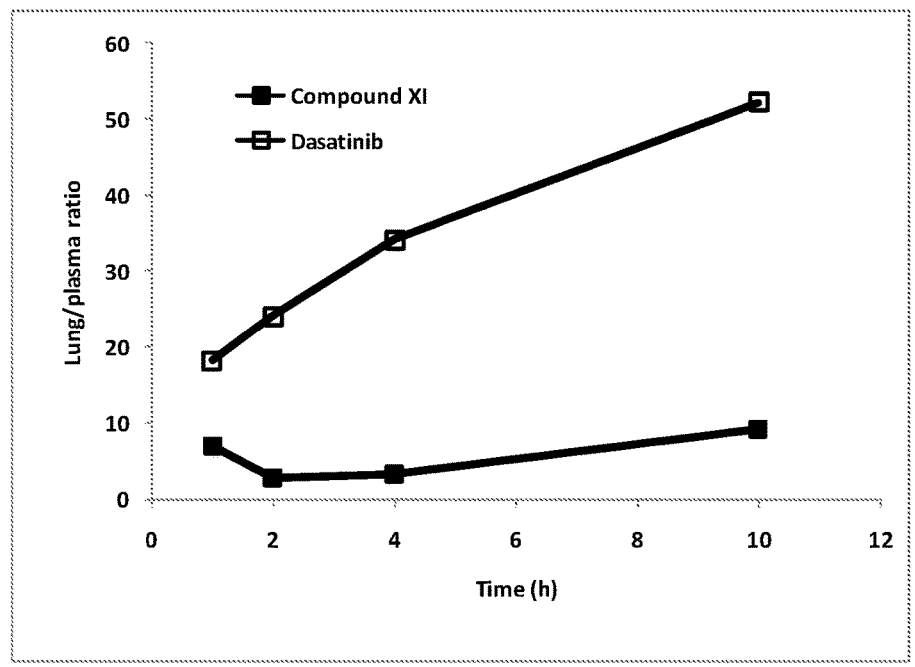
FIG. 5. Mean ratios of lung tissue concentration to plasma concentration versus time for compound XI and dasatinib in mice wherein compound XI and dasatinib were administered together as a single oral dose and each dosed at 5 mg/kg. (2-in-1 dosing, N=3).

Compounds X and XI unexpectedly showed significantly lower ratios for parent compound concentration levels in lung tissue compared to their plasma concentrations as compared to dasatinib at all time points tested (FIGS. 4 and 5). These results show that compounds X and XI distribute less than dasatinib into lung tissue.

Dasatinib is associated with severe respiratory toxicity such as pleural effusion and pulmonary hypertension, which have been attributed to the accumulation of dasatinib in lung tissue. (Quintás-Cardama A et al. Pleural effusion in patients with chronic myelogenous leukemia treated with dasatinib after imatinib failure. J Clin Oncol 2007; 25(25):3908-14; Wang X et al. Differential effects of dosing regimen on the safety and efficacy of dasatinib: retrospective exposure-response analysis of a Phase III study. Clin Pharmacol, 2013; 5: 85-97; Guignabert C et al. Dasatinib induces lung vascular toxicity and predisposes to pulmonary hypertension. J Clin Invest 2016; 126(9):3207-18; Iurlo A, et al. Pleural effusion and molecular response in dasatinib-treated chronic myeloid leukemia patients in a real-life Italian multicenter series. Ann Hematol. 2017; Oct 2. Doi: 10.1007/soo277-017-3144-1).

Therefore, the unexpected significantly lower distribution of compounds X and XI into lung tissue from plasma is suggestive of lower potential of these compounds to accumulate in lung tissue, and therefore, a lower potential for drug-induced lung toxicity as compared to dasatinib.

Combination Therapy

In one aspect, the composition to be administered can include a plurality of different pharmacologically active compounds which can include a plurality of compounds of the invention including one or more compounds of formulas I, II, III, IV, and/or V, preferably one or more of compounds I, II, III, IV, V, VI, VII, VIII, IX, X, XI, XII, XIII, and/or XIV (compounds I-XIV), and more preferably one or more of compounds IV, V, X, and/or XI, including salts, prodrugs, and/or isomers thereof, and other therapeutically effective agents for the same disease or condition, wherein the compounds have an additive or a synergistic effect on the disease indication.

In one preferred aspect, the invention provides methods for treating a kinase dysfunction-mediated disease or condition in an animal or human subject, wherein the method involves administering to the subject an effective amount of one or more compounds having formulas I, II, III, IV, and/or V, preferably one or more of compounds I, II, III, IV, V, VI, VII, VIII, IX, X, XI, XII, XIII, and/or XIV (compounds I-XIV), and more preferably one or more of compounds IV, V, X, and/or XI, salts, prodrugs, and/or isomers thereof, in combination with one or more other therapies for treating the same disease or condition. Other therapies, may include medical procedures (such as surgeries), therapeutic agents, and/or radiation. Therapeutic agents include chemotherapeutic agents, biologics, and immunotherapeutics. Combination therapy can include administration of one or more of compounds described herein with one or more other therapeutics at different times or simultaneous administration. In some embodiments, dosages may be modified for one or more of the compounds of the invention or other therapeutics used in combination, such modifications being a reduction in the dose amounts relative to a compound or therapy used alone.

It is understood that use in combination includes use with other medical procedures, therapeutics, and therapies where the other therapy or drug may be administered at different times, within a short time period, such as within 1, 2, 3, or 4-24 hours, or within a longer time period, such a 1-2 days, 2-4 days, 4-7 days, or 1-4 weeks. Use of the compounds of the invention can be in combination with a medical procedure such as surgery, performed on the subject once or infrequently, where the compounds are administered within a short time or longer time before or after the medical procedure.

Administration

The methods and compounds will typically be used in therapy for human subjects with a kinase-mediated disease or condition. However, they may also be used to treat similar or identical indications in other animal subjects. In this context, the terms "subject" and "animal subject" and the like refer to human and non-human vertebrates, i.e., mammals, such as non-human primates, sports and commercial animals, e.g., equines, bovines, porcines, ovines, rodents, and pets, e.g., canines and felines.

Compounds of formulas I, II, III, IV, and V, preferably compounds I, II, III, IV, V, VI, VII, VIII, IX, X, XI, XII, XIII, and/or XIV, and more preferably compounds IV, V, X, and XI may in some cases form salts which are also within the scope of this invention. The term "salts(s)", as employed herein, denotes acidic and/or basic salts formed with inorganic and/or organic acids and bases.

Exemplary acid addition salts include acetates (such as those formed with acetic acid or trihaloacetic acid, for example trifluoroacetic acid), adipates, alginates, ascorbates, aspartates, benzoates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, 2-hydroxyethanesulfanates, lactates, maleates, methanesulfonates, nicotinates, nitrates, oxalates, pectinates, phosphates, picrates, salicylates, propionates, tartrates, thiocyantes, toluenesulfonates, and the like.

Exemplary basic salts include ammonium salts, alkali metal salts such sodium, lithium, and potassium salts, alkaline earth metal salts such as calcium and magnesium salts, and salts with organic bases (for example organic amines), and the like.

Compounds of formulas I, II, III, IV, and V, including compounds I, II, III, IV, V, VI, VII, VIII, IX, X, XI, XII, XIII, and/or XIV (compounds I-XIV), salts, prodrugs, and/or isomers thereof, can be administered intravenously, intramuscularly, subcutaneously, orally, transdermally, transmucosally, rectally, or by inhalation. In the case of intravenous administration, the dose may be administered as a bolus or infusion.

Pharmaceutical compositions for oral use can be obtained, for example, by combining one or more compounds of formula I, II, III, IV, and/or V, preferably one or more of compounds I, II, III, IV, V, VI, VII, VIII, IX, X, XI, XII, XIII, and/or XIV, and more preferably one or more of compounds IV, V, X, and/or XI, salts, prodrugs, and/or isomers thereof, with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethylcellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

For injection, the compounds of formula I, II, III, IV, and V, preferably compounds I, II, III, IV, V, VI, VII, VIII, IX, X, XI, XII, XIII and XIV, and more preferably compounds IV, V, X, and XI, salts, prodrugs, and/or isomers thereof, are formulated in sterile liquid solutions, preferably in physically compatible buffers or solutions, such as saline solution, Hank's solution, or Ringer's solution. In addition, the compounds may be formulated in solid form and re-dissolved or suspended immediately prior to use. Lyophilized forms can also be produced.

The administration of the compounds described herein can occur simultaneously or sequentially with chemotherapy or radiation. It is understood that administration of other therapeutics or drugs to treat a medical disease or condition can be by a different route of administration or by the same route of administration.

In another aspect, the use in combination therapy for any route of administration includes delivery of compounds of the invention and one or more other drug therapeutics delivered by the same route of administration together in any formulation, or administered together, within 1 hour, 2 hours, 3 hours, up to 24 hours, in separate formulations, or by different routes of administration.

The invention also provides for a pharmaceutical combination, e.g., a kit, comprising (a) a first agent which is a compound of the invention as disclosed herein, in free form or in pharmaceutically acceptable salt form, and (b) at least one co-agent. The kit can include instructions for administration.

General Synthetic Methods

The present invention also includes processes for the preparation of the novel deuterium-enriched and non-enriched compounds of the invention. In the reactions described, it can be necessary to protect reactive functional groups, for example hydroxy, amino, imino, thio, or carboxy groups, where these are desired in the final product, to avoid their unwanted participation in the reactions. Conventional protecting groups can be used in accordance with standard practice, for example, see T W Greene and P G M Wuts in *Protective Groups in Organic Chemistry*, John Wiley and Sons, 1991.

Compounds of formulas I, II, III, IV, and V, including the exemplary compounds, can generally be synthesized by making appropriate modifications to reagents of scheme 1 (and other applicable schemes) below as would be understood by the person of ordinary skill in the art. It is noted that non-deuterated intermediates are generally commercially available and so the synthesis could be started, for example, at compound 7 (see e.g. compound 7H in schemes 8-14) using the appropriate commercially available intermediate.

Compound I can be synthesized by the method shown in Scheme 1.

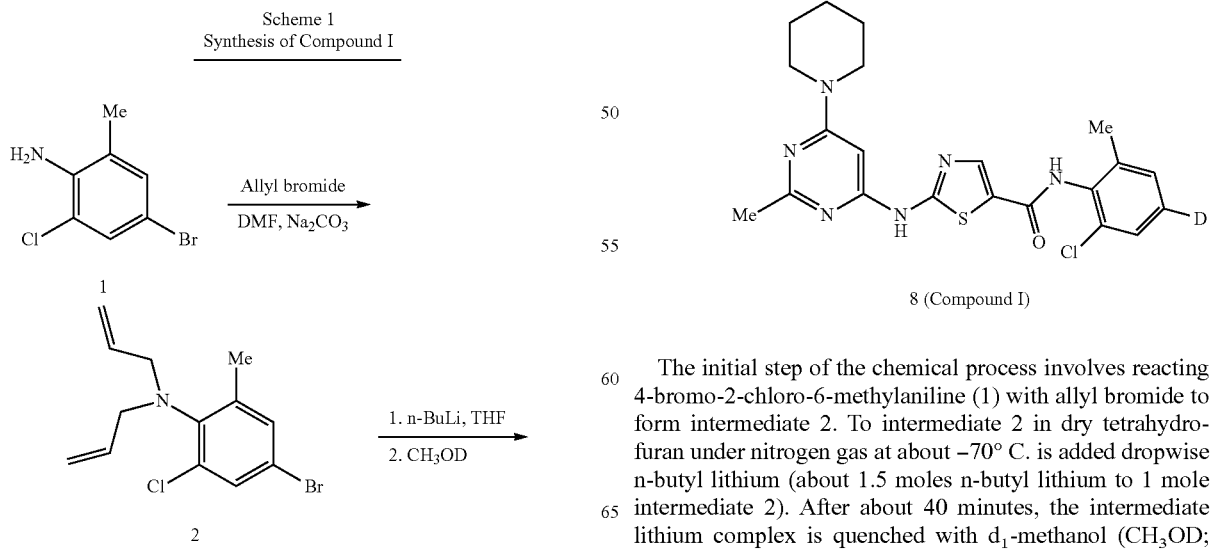

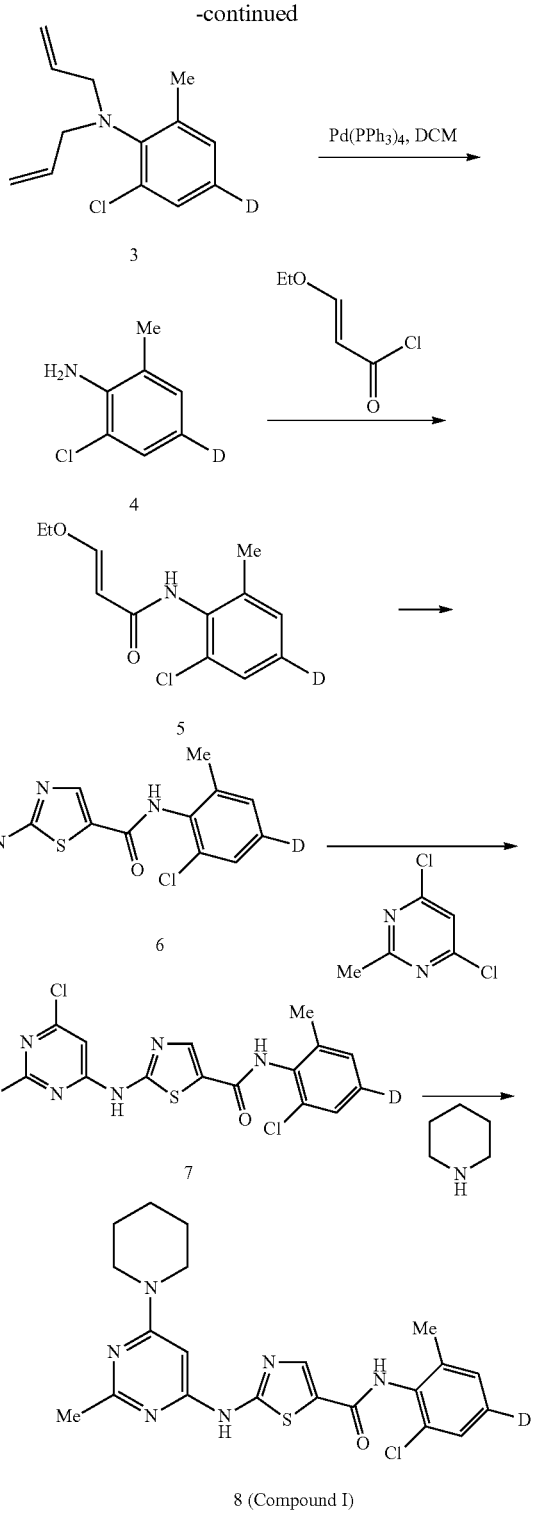

The initial step of the chemical process involves reacting 4-bromo-2-chloro-6-methylaniline (1) with allyl bromide to form intermediate 2. To intermediate 2 in dry tetrahydrofuran under nitrogen gas at about −70° C. is added dropwise n-butyl lithium (about 1.5 moles n-butyl lithium to 1 mole intermediate 2). After about 40 minutes, the intermediate lithium complex is quenched with $d_1$-methanol ($CH_3OD$; 99% deuterium, #550574; Lot #MKBW0355V, Aldrich, St Louis, Mo.) to selectively incorporate deuterium at the 4 position and give intermediate 3. The allyl protecting groups are removed by standard procedure to give the aniline intermediate 4. Intermediate 4 is reacted with 3-ethoxyacryloyl chloride to form the acrylamide intermediate 5 which is then treated with N-bromosuccinimide and thiourea to form the thiazole intermediate 6. The thiazole intermediate 6 is treated with the base sodium hydride followed by addition of 4,6-dichloro-2-methylpyrimidine to form the 2-[(6-chloro-2-methylpyrimidin-4-yl)amino]-N-(2-chloro-4-deutero-6-methylphenyl)thiazole-5-carboxamide (intermediate 7). Intermediate 7 is reacted with piperidine and N,N-diisopropylethylamine to form the desired product compound I (8).

Compound II can be synthesized by the method shown in Scheme 2.

Scheme 2
Synthesis of compound II

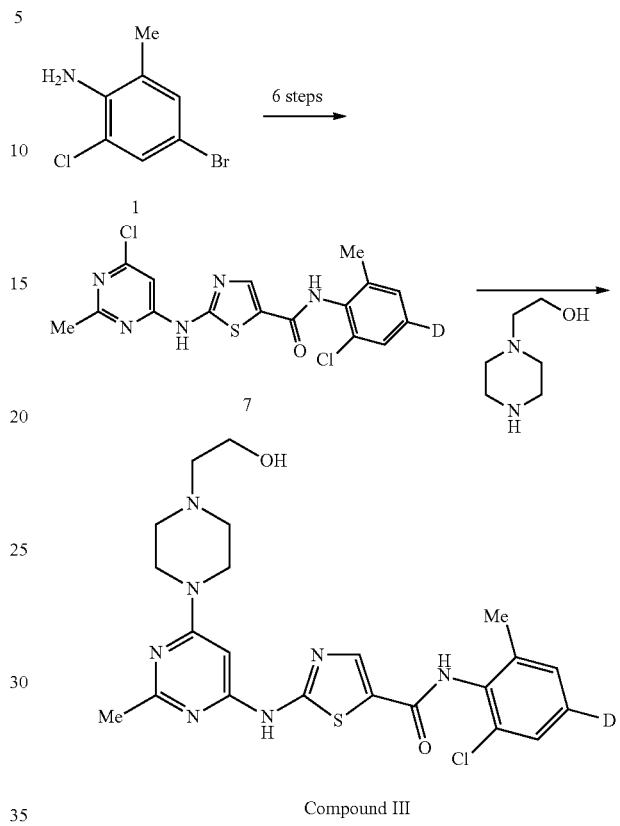

Scheme 3
Synthesis of compound III

In the synthesis of compound III, the first 6 steps in the method are identical to those used in the synthesis of compound I to produce intermediate 7. The last step in the synthesis uses 1-(2-hydroxyethyl)piperazine (Sigma-Aldrich; St Louis, Mo.) and N,N-diisopropylethylamine to react with intermediate 7 to form the desired addition product compound III.

Compound IV can be synthesized by the method shown in Scheme 4.

Scheme 4
Synthesis of compound IV

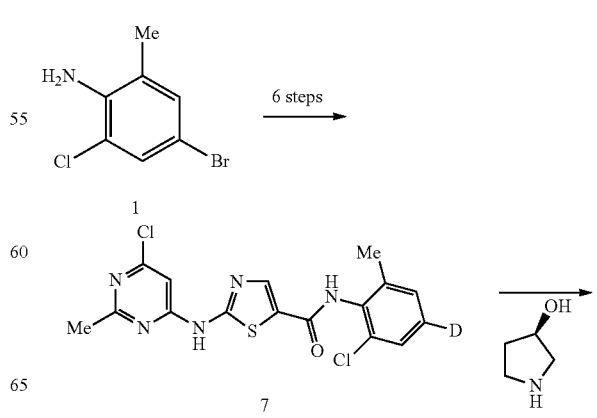

In the synthesis of compound II, the first 6 steps in the method are identical to those used in the synthesis of compound I to produce intermediate 7. The last step in the synthesis uses 4-hydroxypiperidine and N,N-diisopropylethylamine to react with intermediate 7 to form the desired product compound II.

Compound III can be synthesized by the method shown in Scheme 3.

-continued

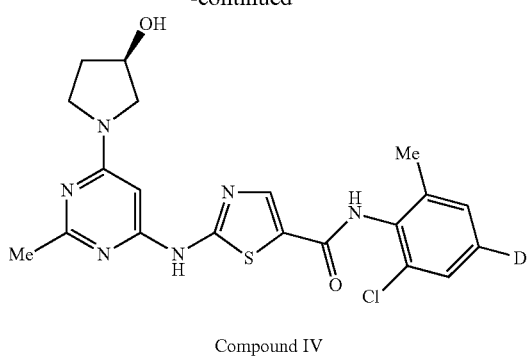

Compound IV

In the synthesis of compound IV, the first 6 steps in the method are identical to those used in the synthesis of compound I to produce intermediate 7. Intermediate 7 is react with (S)-3-hydroxypyrrolidine and N,N-diisopropylethylamine to form the desired product compound IV.

Compound V can be synthesized by the method shown in Scheme 5.

Scheme 5
Synthesis of compound V

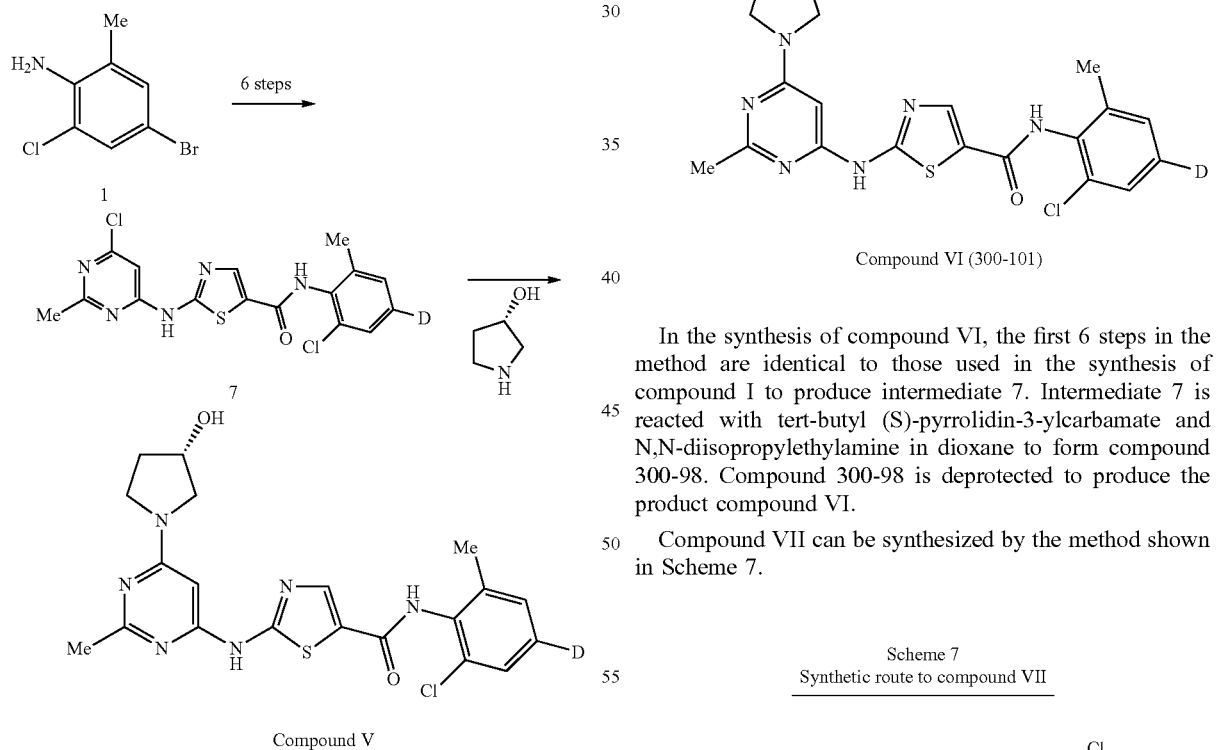

Compound V

In the synthesis of compound V, the first 6 steps in the method are identical to those used in the synthesis of compound I to produce intermediate 7. Intermediate 7 is reacted with (R)-3-hydroxypyrrolidine and N,N-diisopropylethylamine to form the desired product compound V.

Compound VI can be synthesized by the method shown in Scheme 6.

Scheme 6
Synthetic route to compound VI

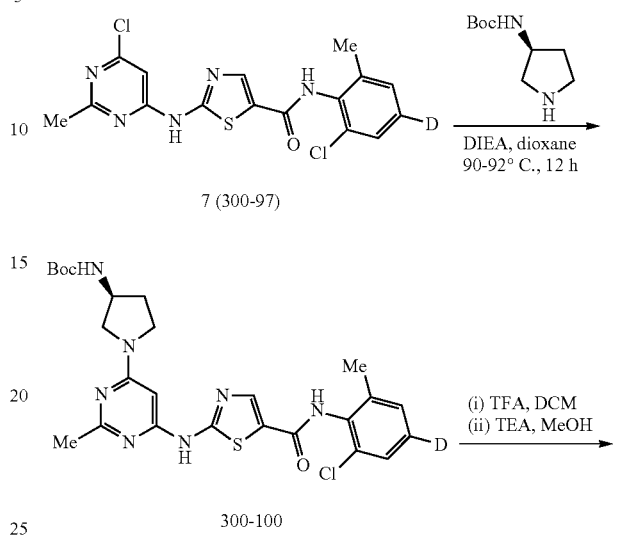

Compound VI (300-101)

In the synthesis of compound VI, the first 6 steps in the method are identical to those used in the synthesis of compound I to produce intermediate 7. Intermediate 7 is reacted with tert-butyl (S)-pyrrolidin-3-ylcarbamate and N,N-diisopropylethylamine in dioxane to form compound 300-98. Compound 300-98 is deprotected to produce the product compound VI.

Compound VII can be synthesized by the method shown in Scheme 7.

Scheme 7
Synthetic route to compound VII

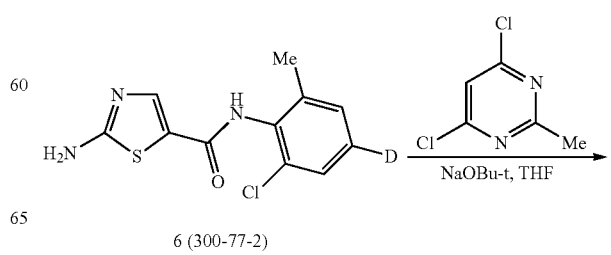

6 (300-77-2)

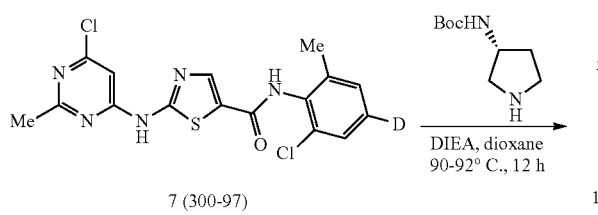

7 (300-97)

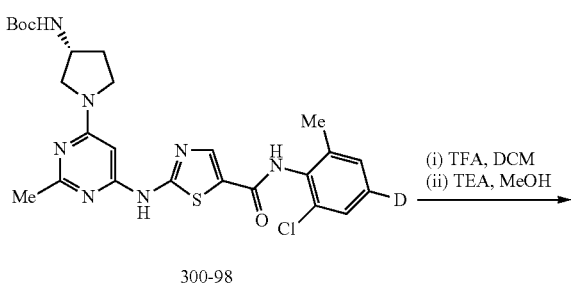

300-98

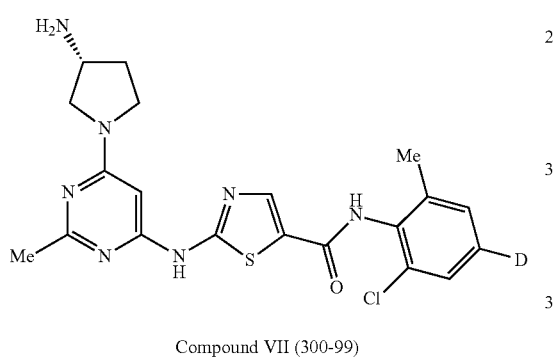

Compound VII (300-99)

In the synthesis of compound VII, the first 6 steps in the method are identical to those used in the synthesis of compound I to produce intermediate 7. Intermediate 7 is reacted with tert-butyl (R)-pyrrolidin-3-ylcarbamate and N,N-diisopropylethylamine in dioxane to form compound 300-100. Compound 300-100 is deprotected to produce the product compound VII.

Compound VIII can be synthesized by the method shown in Scheme 8.

Scheme 8
Synthetic route for Compound VIII

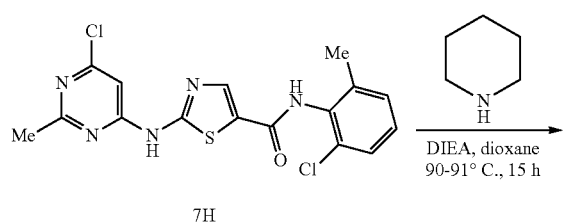

7H

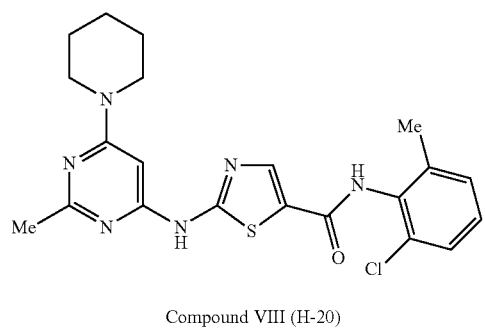

Compound VIII (H-20)

In the synthesis of compound VIII, commercially available intermediate 7H (Combi-Blocks, Inc., San Diego, Calif.) is reacted with piperidine and N,N-diisopropylethylamine in dioxane to form the desired product compound VIII.

Compound IX can be synthesized by the method shown in Scheme 9.

Scheme 9
Synthetic route for Compound IX

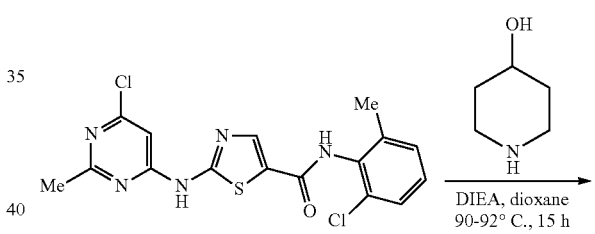

7H

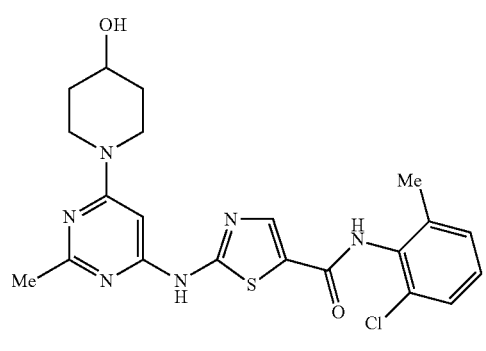

Compound IX (H-21)

In the synthesis of compound IX, commercially available intermediate 7H is reacted with 4-hydroxypiperidine and N,N-diisopropylethylamine in dioxane to form the desired product compound IX.

Compound X can be synthesized by the method shown in Scheme 10.

Scheme 10
Synthetic route for Compound X (H-31)

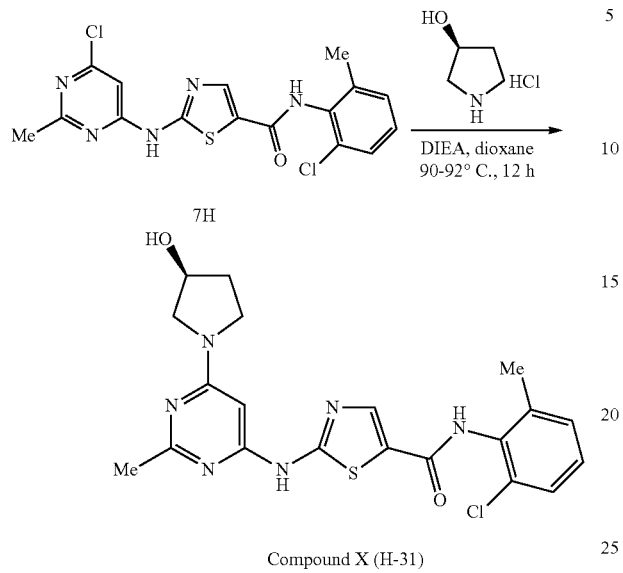

Compound X (H-31)

In the synthesis of compound X, commercially available intermediate 7H is reacted with (S)-pyrrolidin-3-ol hydrochloride and N,N-diisopropylethylamine in dioxane to form the desired product compound X.

Compound XI can be synthesized by the method shown in Scheme 11.

Scheme 11
Synthetic route for Compound XI (H-30)

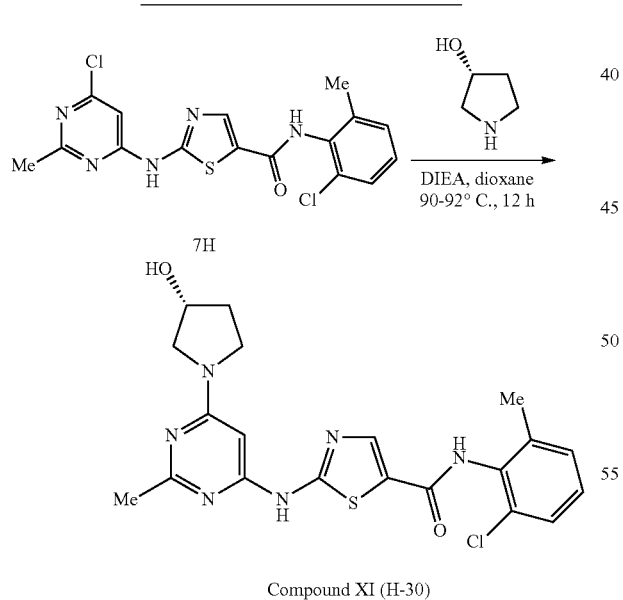

Compound XI (H-30)

In the synthesis of compound X, commercially available intermediate 7H is reacted with (R)-pyrrolidin-3-olhydrochloride and N,N-diisopropylethylamine in dioxane to form the desired product compound XI.

Compound XII can be synthesized by the method shown in Scheme 12.

Scheme 12
Synthetic route for Compound XII

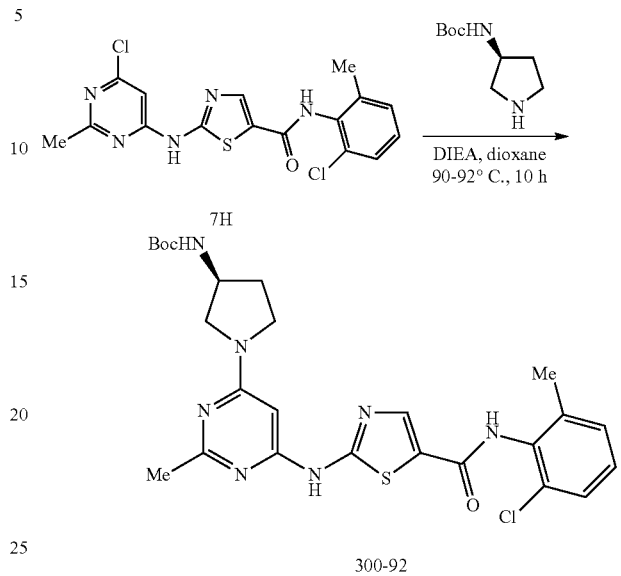

Compound XII (H-41)

In the synthesis of compound XII, commercially available intermediate 7H is reacted with tert-butyl (S)-pyrrolidin-3-ylcarbamate and N,N-diisopropylethylamine in dioxane to form intermediate 300-92. Intermediate 300-92 is deprotected to produce compound XII.

Compound XIII can be synthesized by the method shown in Scheme 13.

Scheme 13
Synthetic route for Compound XIII

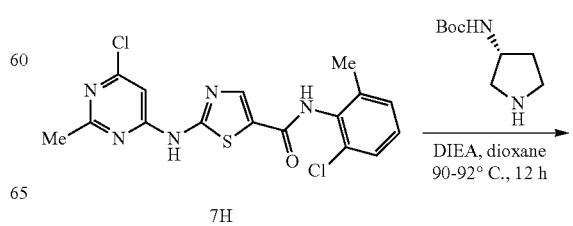

7H

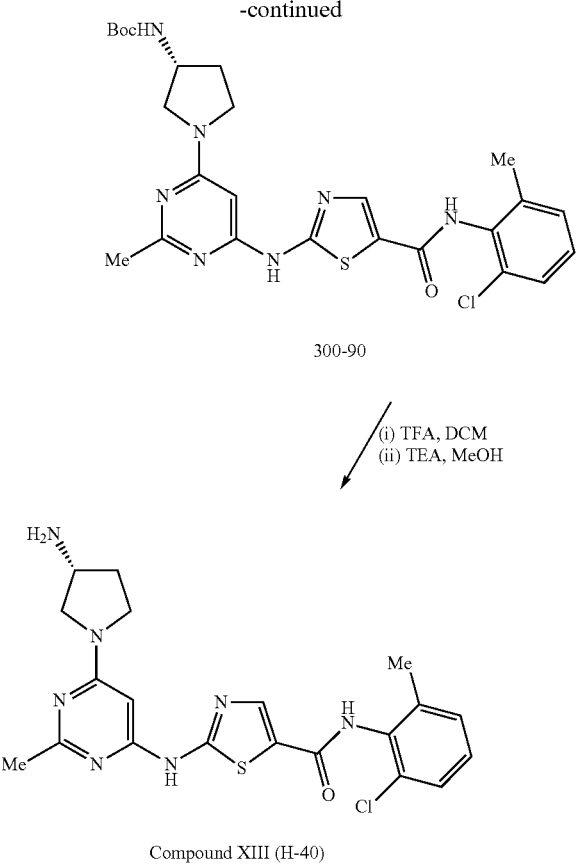

300-90

(i) TFA, DCM
(ii) TEA, MeOH

Compound XIII (H-40)

In the synthesis of compound XIII, commercially available intermediate 7H is reacted with tert-butyl (R)-pyrrolidin-3-ylcarbamate and N,N-diisopropylethylamine in dioxane to form intermediate 300-92. Intermediate 300-92 is deprotected to produce compound XII.

Compound XIV can be synthesized by the method shown in Scheme 14.

Scheme 14
Synthetic route for Compound XIV

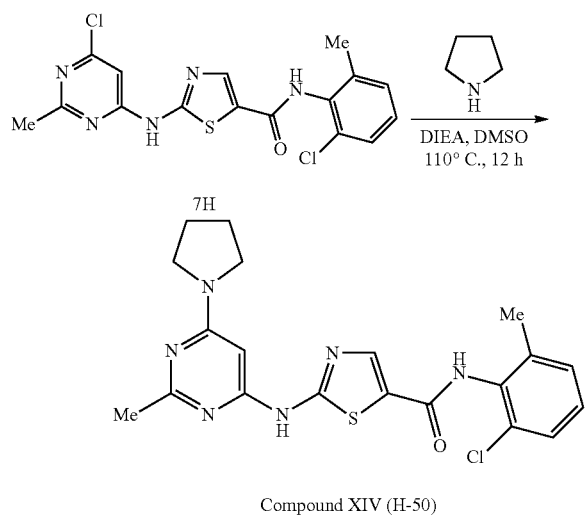

Compound XIV (H-50)

In the synthesis of compound XIV, commercially available intermediate 7H is reacted with pyrrolidine and N,N-diisopropylethylamine in dimethyl sulfoxide (DMSO) to form compound XIV.

EXAMPLES

Examples related to the present invention are described below. In more cases, alternative techniques can be used. The examples are intended to be illustrative and are not limiting or restrictive to the scope of the invention. In some examples, the mass spectrometry results indicated that a compound may have more than one value due to the isotope distribution of an atom in the molecule, such as a compound having a bromo or chloro substituent.

Example 1

Synthesis of N-(2-chloro-4-deuterio-6-methyl-phenyl)-2-[[2-methyl-6-(1-piperidyl)pyrimidin-4-yl]amino]thiazole-5-carboxamide (Compound I)

Preparation of N,N-diallyl-4-bromo-2-chloro-6-methylaniline (2): To a 250 mL flask were added 4-bromo-2-chloro-6-methylaniline (3 g, 13.61 mmol), dimethyl formamide (DMF) (50 mL), and sodium carbonate (6.37 g, 60.09 mmol, 4.4 eq) at 0° C. With stirring, allyl bromide (9.4 mL, 108.62 mmol, 8 eq) was added dropwise at 0-5° C. under nitrogen. After addition, the mixture was stirred at room temperature for 20 min and heated at 120° C. under nitrogen for 3 h when TLC analysis showed no presence of the starting material. The mixture was then cooled to room temperature and poured into cold water followed by extraction with ethyl acetate (EtOAc) (2×150 mL). The combined organic layers were washed with brine (3×100 mL), dried (sodium sulfate, $Na_2SO_4$), and concentrated under reduced pressure to get a black-brown liquid residue, which was purified by column chromatography (hexanes only) to give compound 2 (3.9 g, 95%) as a pale brown liquid.

Preparation of N,N-diallyl-2-chloro-4-deutero-6-methylaniline (3): To a solution of compound 2 (2 g, 6.65 mmol) in tetrahydrofuran (THF) (40 mL) at −70° C. under nitrogen was added 2.5 M solution of n-butyl lithium (4 ml, 10 mmol) dropwise. After addition, the mixture was stirred at −70° C. for 40 min and then quenched by addition of deuterated methanol (MeOD) (2 mL, 49.2 mmol, 99% deuterium, #550574; Lot # MKBW0355V, Aldrich, St Louis, Mo.) dropwise. The reaction mixture was then stirred from −70° C. to −20° C. over 40 min when thin layer chromatograph (TLC) analysis (hexanes only) showed the reaction was complete. The mixture was poured into cold water (100 mL) followed by extraction with EtOAc (2×100 mL). The combined organic layers were washed with brine, dried ($Na_2SO_4$), and concentrated under reduced pressure. The residue was purified by column chromatography (hexanes only, then EtOAc:hexanes; 1:20) to give compound 3 (1.38 g, 93%) as a pale yellow liquid. $^1H$ Nuclear magnetic resonance (NMR) ($CDCl_3$): 7.20 (s, 1H), 7.09 (s, 1H), 5.95 (m, 2H), 5.21-5.20 (m, 4H), 3.79 (d, 4H), 2.41 (s, 3H). $^1H$ NMR showed absence of the proton signal at the 4 position of compound 3.

Preparation of 2-chloro-4-deutero-6-methylaniline (4): To a stirring solution of the aniline 3 (3 g, 13.31 mmol) in DCM (130 mL) were added N,N.dimethylbarbituric acid (8.3 g, 53.16 mmol, 4 eq) and $Pd(PPh_3)_4$ (0.5 g, 0.43 mmol, 0.032 eq). The mixture was heated at reflux under nitrogen for 4 h. TLC analysis (EtOAc:hexanes; 1:9) showed the reaction was complete. After the mixture was cooled to room temperature and concentrated under reduced pressure. The residue was dissolved in EtOAc (120 mL) and the organic layer was washed with 10% sodium bicarbonate (NaHCO$_3$) solution (4×60 mL), dried (Na$_2$SO$_4$), and concentrated. The crude product was purified by column chromatography (EtOAc:hexanes; 1:9) to give the desired aniline 4 (1.67 g, 88%) as a pale brown liquid.

Preparation of N-(2-chloro-4-deutero-6-methylphenyl)-3-ethoxyacrylamide (5): To a mixture of compound 4 (460 mg, 3.23 mmol), pyridine (0.4 mL, 4.95 mmol, 1.5 eq), and THF (25 mL) at 0-5° C. was added 3-ethoxyacryloyl chloride (666 mg, 4.95 mmol, 1.5 eq) dropwise. After addition, the mixture was stirred at room temperature under nitrogen overnight. TLC analysis (EtOAc:hexanes; 1:2) showed absence of starting material. EtOAc (80 mL) and water (80 mL) were added to the mixture and the organic layer separated and washed with 1N hydrochloric acid (HCl) solution, water, and 5% NaHCO$_3$ solution, dried (Na$_2$SO$_4$), and concentrated to give the compound 5 as a white solid, which was used in the next step without purification.

Preparation of 2-amino-N-(2-chloro-4-deutero-6-methylphenyl)thiazole-5-carboxamide (6): To a mixture of the acrylamide 5 (900 mg, 3.74 mmol), 1,4-dioxane(7 mL), and water (7 mL) was added N-bromosuccinimide (730 mg, 4.10 mmol, 1.1 eq) at 0° C. The slurry was stirred at room temperature for 3 h. Thiourea (285 mg, 3.75 mmol, 1 eq) was added and the mixture heated to 80° C. After 3 h, the mixture was cooled to room temperature followed by addition of concentrated ammonium hydroxide solution (1 mL). After stirring, EtOAc (80 mL) and water (80 mL) were added to the mixture. The organic layer was separated and the aqueous layer was extracted with EtOAc (80 mL). The combined organic layers were washed with water, dried (Na$_2$SO$_4$), and concentrated. The residue was subjected to column chromatography (EtOAc-hexanes, 1:4 to 1:2) to give compound 6 (0.82 g, 82%) as a pale brown solid. Liquid chromatography-mass spectrometry (LC-MS) analysis showed a protonated parent ion at 269.14 (M+H).

Preparation of 2-[(6-chloro-2-methylpyrimidin-4-yl)amino]-N-(2-chloro-4-deutero-6-methylphenyl)thiazole-5-carboxamide (7): To a mixture of sodium hydride (60%, 67 mg, 1.67 mmol) and THF (15 mL) at 0° C. was added compound 6 (150 mg, 0.56 mmol) in portions. The mixture was stirred at 0° C. for 30 min and a solution of 4,6-dichloro-2-methylpyrimidine (109 mg, 0.67 mmol, 1.2 eq) was added dropwise. The resulting mixture was stirred at room temperature for 3 h when LC-MS analysis showing absence of starting material. The mixture was concentrated to provide the crude compound 7, which was used in next step without purification.

Preparation of N-(2-chloro-4-deutero-6-methylphenyl)-2-[[2-methyl-6-(piperdin-1-yl)pyrimidin-4-yl]amino]thiazole-5-carboxamide (8, compound I): To a mixture of the crude compound 7 (about 0.56 mmol) in dioxane (10 mL) was added piperidine (143 mg, 1.68 mmol, 3 eq) and N,N-diisopropylethylamine (DIEA) (217 mg, 1.68 mmol, 3 eq) at room temperature. The mixture was stirred at 85-90° C. under nitrogen for 20 h. LC-MS analysis showed the product peak. The mixture was not a clear solution. The mixture was concentrated to dryness and suspended in 50 mL acetonitrile containing 20% HPLC grade water. The mixture was then centrifuged at 4000 rpm for 15 minutes. The pellet was re-suspended in acetonitrile and centrifuged again at 4000 rpm for 15 minutes. The final pellet was dried under nitrogen, and recovered as an off-white solid of the target Compound I (compound 8) (12 mg). The purity of the final product was determined to be greater than 95% by liquid chromatograph-ultraviolet-mass spectrometry (LC-UV-MS). LC-MS: 444.14 (M+H); $^1$H NMR (DMSO-d$_6$): 11.52 (s, 1H. NH), 9.82 (s, 1H, NH), 8.18 (s, 1H), 7.39 (s, 1H), 7.21 (s, 1H), 6.00 (s, 1H), 3.55 (m, 4H), 3.22 (s, 3H), 2.43 (s, 3H), 1.65 (m, 6H). $^1$H NMR showed absence of a proton signal at the 4-position of compound I.

Example 2

Preparation of N-(2-chloro-4-deuterio-6-methylphenyl)-2-[[6-(4-hydroxy-1-piperidyl)-2-methylpyrimidin-4-yl]amino]thiazole-5-carboxamide (Compound II)

Compound II was synthesized starting from 2-[(6-chloro-2-methylpyrimidin-4-yl)amino]-N-(2-chloro-4-deutero-6-methylphenyl)thiazole-5-carboxamide (7) by the synthetic procedure shown in Scheme 2.

2-[(6-chloro-2-methylpyrimidin-4-yl)amino]-N-(2-chloro-4-deutero-6methylphenyl)thiazole-5-carboxamide (7) was prepared in six steps starting from 4-bromo-2-chloro-6-methylaniline as described in Example 1.

Preparation of N-(2-chloro-4-deutero-6-methylphenyl)-2-[[2-methyl-6-(4-hydroxypiperidin-1-yl)pyrimidin-4-yl]amino]thiazole-5-carboxamide (compound II): To a mixture of the crude compound 7 (about 0.56 mmol) in dioxane (10 mL) was added 4-hydroxypiperidine (170 mg, 1.68 mmol, 3 eq) and DIEA (217 mg, 1.68 mmol, 3 eq) at room temperature. The mixture was stirred at 85-90° C. under nitrogen for 20 h. LC-MS analysis showed the product peak. The mixture was not a clear solution. The mixture was concentrated to dryness followed by suspending in 50 mL acetonitrile. The mixture was centrifuged at 4000 rpm for 15 min. The pellet was dissolved in methanol, and purified with column chromatography (methanol-methylene chloride, 1:9). The column chromatograph fractions containing only compound II were combined and dried under a nitrogen flow and recovered as an off-white solid of the target compound II (17 mg). The purity of the final product was determined to be greater than 95% by LC-UV-MS. LC-MS: 460.14 (M+H); $^1$H NMR (DMSO-d$_6$): 11.42 (s, 1H. NH), 9.83 (s, 1H, NH), 8.19 (s, 1H), 7.40 (s, 1H), 7.24 (s, 1H), 6.05 (s, 1H), 4.78 (s, 1H), 3.95 (m, 2H), 3.75 (m, 1H), 3.22 (s, 3H), 3.18 (m, 2H), 2.43 (s, 3H), 1.85 (m, 2H), 1.35 (m, 2H). $^1$H NMR showed absence of a proton signal at the 4-position of compound II.

Example 3

Preparation of N-(2-chloro-4-deutero-6-methylphenyl)-2-[[2-methyl-6-(4-(2-hydroxyethyl)piperidin-1-yl)pyrimidin-4-yl]amino]thiazole-5-carboxamide (Compound III)

To a mixture of the crude compound 7 (about 0.56 mmol) and dioxane (10 mL) were added 4-(2-hydroxyethyl)piperidine (219 mg, 1.68 mmol, 3 eq) and DIEA (217 mg, 1.68 mmol, 3 eq) at room temperature. The mixture was then stirred at 85-90° C. under nitrogen for 20 h. LC-MS analysis showed the product peak. The mixture was not a clear solution. The mixture was cooled to room temperature, concentrated under reduced pressure to dryness, and suspended in 50 mL acetonitrile containing 20% HPLC grade water. The mixture was then centrifuged at 4000 rpm for 15 min. The pellet was re-suspended in acetonitrile and centrifuged again at 4000 rpm for 15 min. The final pellet was dried under nitrogen, and recovered as an off-white solid of the target compound III (about 40 mg) as an off-white solid. LC-MS: 489.16 (M+H); $^1$H NMR (DMSO-d$_6$): 11.42 (s, 1H. NH), 9.83 (s, 1H, NH), 8.20 (s, 1H), 7.40 (s, 1H), 7.24 (s, 1H), 6.05 (s, 1H), 4.42 (m, 1H), 3.35 (m, 2H), 2.48 (m, 8H), 2.40 (s, 3H), 2.15 (m, 2H).

Example 4

Preparation of N-(2-chloro-4-deutero-6-methylphenyl)-2-[[2-methyl-6-((S)-3-hydroxypyrrolidin-1-yl)pyrimidin-4-yl]amino]thiazole-5-carboxamide (Compound IV)

To a mixture of the crude compound 7 (about 0.56 mmol) and dioxane (10 mL) were added (S)-pyrrolidin-3-ol hydrochloride (208 mg, 1.68 mmol, 3 eq) and DIEA (400 mg, 3.1 mmol, 5.5 eq) at room temperature. The mixture was then stirred at 85-90° C. under nitrogen for 6 h. LC-MS analysis showed the product peak. The mixture was not a clear solution. The mixture was cooled to room temperature and concentrated to dryness under reduced pressure, and the resultant residue was suspended in 50 mL acetonitrile, and centrifuged at 4000 rpm for 15 min. The pellet was then suspended in cooled 80% acetonitrile, and centrifuged at 4000 rpm for 15 min. The pellet was re-suspended in cooled 80% acetonitrile, and centrifuged at 4000 rpm for 15 min. The supernatants were combined and concentrated to dryness to afford the target compound IV (about 60 mg) as an off-white solid. LC-MS: 446 (M+H); $^1$H NMR (DMSO-d$_6$): 11.40 (s, 1H. NH), 9.83 (s, 1H, NH), 8.19 (s, 1H), 7.40 (s, 1H), 7.24 (s, 1H), 5.80 (s, 1H), 4.98 (s, 1H), 4.35 (s, 1H), 2.53 (s, 3H), 2.20 (s, 2H), 2.12 (s, 2H), 1.85 (m, 2H).

Example 5

Preparation of N-(2-chloro-4-deutero-6-methylphenyl)-2-[[2-methyl-6-((R)-3-hydroxypyrrolidin-1-yl)pyrimidin-4-yl]amino]thiazole-5-carboxamide (Compound V)

To a mixture of the crude compound 7 (about 0.56 mmol) and dioxane (10 mL) were added (R)-pyrrolidin-3-ol hydrochloride (208 mg, 1.68 mmol, 3 eq) and DIEA (400 mg, 3.1 mmol, 5.5 eq) at room temperature. The mixture was then stirred at 85-90° C. under nitrogen for 6 h. LC-MS analysis showed the product peak. The mixture was not a clear solution. The mixture was cooled to room temperature and concentrated to dryness under reduced pressure, and the resultant residue was suspended in 50 mL acetonitrile, and centrifuged at 4000 rpm for 15 min. The pellet was then suspended in cooled 80% acetonitrile, and centrifuged at 4000 rpm for 15 min. The pellet was re-suspended in cooled 80% acetonitrile, and centrifuged at 4000 rpm for 15 min. The supernatants were combined and concentrated to dryness to afford the target compound V (about 103 mg) as an off-white solid. LC-MS: 446 (M+H); $^1$H NMR (DMSO-d$_6$): 11.40 (s, 1H. NH), 9.83 (s, 1H, NH), 8.19 (s, 1H), 7.40 (s, 1H), 7.24 (s, 1H), 5.80 (s, 1H), 4.98 (s, 1H), 4.35 (s, 1H), 2.53 (s, 3H), 2.20 (s, 2H), 2.12 (s, 2H), 1.85 (m, 2H).

Example 6

Preparation of N-(2-chloro-4-deutero-6-methylphenyl)-2-[[2-methyl-6-((S)-3-aminopyrrolidin-1-yl)pyrimidin-4-yl]amino]thiazole-5-carboxamide (Compound VI, 300-101)

Preparation of N-(2-chloro-4-deutero-6-methylphenyl)-2-[[2-methyl-6-((S)-3 aminopyrrolidin-1-yl)pyrimidin-4-yl] amino]thiazole-5-carboxamide (Compound VII, 300-101). To a mixture of 300-97 (200 mg, 0.51 mmol) and dioxane (8 mL) were added tert-butyl (S)-pyrrolidin-3-ylcarbamate (186 mg, 1 mmol, 2 eq) and DIEA (147 mg, 1.14 mmol, 2 eq) at room temperature. The mixture was then stirred at 90-91° C. under nitrogen for 12 h. LC-MS analysis showed the product peak. The mixture was cooled to room temperature and concentrated under reduced pressure, after addition of methanol (4 mL), the mixture was re-concentrated to give the intermediate 300-100 as a grey solid. LC-MS: 545.12 (M+H).

To the crude sample (300-100) was added DCM (4 mL). The mixture was cooled to 5° C., and then a mixture of TFA-DCM (1:1, 5 mL) was added dropwise. After addition, the mixture was stirred at room temperature for 3 h and concentrated under reduced pressure. The residue was mixed with methanol (4 mL), followed by addition of triethylamine (2 mL) and stirring a while. The mixture was concentrated to dryness, then suspended in 50 mL distilled water, and centrifuged at 4000 rpm for 15 min. The pellet was re-suspended with 50 mL distilled water, and then centrifuged at 4000 rpm for 15 min. The pellet was further suspended with 100 mL 80% acetonitrile, and centrifuged at 4000 rpm for 15 min. The supernatant was evaporated to dryness to afford the target compound VI (300-101) (approximately 108 mg) as an off-white solid. LC-MS: 445 (M+H); $^1$H NMR (DMSO-d$_6$): 9.83 (s, 1H, NH), 8.19 (s, 1H), 7.30 (s, 1H), 7.19 (s, 1H), 5.80 (s, 1H), 3.60-3.35 (m, 2H), 2.43 (s, 3H), 2.20 (s, 2H), 2.12 (s, 2H), 1.85 (m, 2H).

Example 7

Preparation of N-(2-chloro-4-deutero-6-methylphenyl)-2-[[2-methyl-6-((R)-3-aminopyrrolidin-1-yl)pyrimidin-4-yl]amino]thiazole-5-carboxamide (Compound VII, 300-99)

Preparation of 2-[(6-chloro-2-methylpyrimidin-4-yl)amino]-N-(2-chloro-4-deutero-6-methylphenyl)thiazole-5-carboxamide (300-97). To a stirred mixture of the starting material 300-77-2 (200 mg, 0.74 mmol), 4,6-dichloro-2-methylpyrimidine (147 mg, 0.90 mmol, 1.2 eq), and THF (4 mL) was added a solution of sodium tertiary-butoxide in THF (2M, 1.31 mL, 2.62 mmol, 3.5 eq) dropwise at 0-5° C. After addition, the mixture was stirred at room temperature for 1.5 h and re-cooled to 0-5° C. 2N HCl solution (1 mL) was added dropwise. The mixture was stirred for 15 min and concentrated under reduced pressure. The residue was mixed with EtOAc-hexane (1:1) and stirred for 5 min. The solid was filtered and washed with EtOA-hexane (1:1) and dried to give a yellow solid (210 mg), which was used in the next step without purification. LC-MS: 395.03 (M+H).

Preparation of N-(2-chloro-4-deutero-6-methylphenyl)-2-[[2-methyl-6-((R)-3-aminopyrrolidin-1-yl)pyrimidin-4-yl]amino]thiazole-5-carboxamide (Compound VI, 300-99). To a mixture of 300-97 (200 mg, 0.51 mmol) and dioxane (8 mL) were added tert-butyl (R)-pyrrolidin-3-ylcarbamate (186 mg, 1 mmol, 2 eq) and DIEA (147 mg, 1.14 mmol, 2 eq) at room temperature. The mixture was then stirred at 90-91° C. under nitrogen for 12 h. LC-MS analysis showed the product peak. The mixture was cooled to room temperature and concentrated under reduced pressure. After addition of methanol (4 mL), the mixture was re-concentrated to give the intermediate 300-98 as a grey solid. LC-MS: 545.12 (M+H).

To the crude sample (300-98) was added dichloromethane (DCM) (4 mL). The mixture was cooled to 5° C., and then a mixture of trifluoroacetic acid (TFA)-DCM (1:1, 5 mL) was added dropwise. After addition, the mixture was stirred at room temperature for 3 h and concentrated under reduced pressure. The residue was mixed with methanol (4 mL), followed by addition of triethylamine (2 mL) and stirred. The mixture was concentrated to dryness, then suspended in 50 mL distilled water, and centrifuged at 4000 rpm for 15 min. The pellet was re-suspended with 50 mL distilled water, and then centrifuged at 4000 rpm for 15 min. The pellet was further suspended with 100 mL 80% acetonitrile, and centrifuged at 4000 rpm for 15 min. The supernatant was evaporated to dryness to afford the target compound VII (300-99) as an off-white solid (~105 mg). LC-MS: 445 (M+H); $^1$H NMR (DMSO-d$_6$): 9.83 (s, 1H, NH), 8.19 (s, 1H), 7.30 (s, 1H), 7.19 (s, 1H), 5.80 (s, 1H), 3.60-3.35 (m, 2H), 2.43 (s, 3H), 2.20 (s, 2H), 2.12 (s, 2H), 1.85 (m, 2H).

Example 8

Preparation of N-(2-chloro-6-methylphenyl)-2-[[2-methyl-6-(piperidin-1-yl)pyrimidin-4-yl]amino]thiazole-5-carboxamide (Compound VIII, H-20)

Preparation of N-(2-chloro-6-methylphenyl)-2-[[2-methyl-6-(piperidin-1-yl)pyrimidin-4-yl]amino]thiazole-5-carboxamide (Compound VIII, H-20). To a mixture of the starting material 7H (150 mg, 0.38 mmol), dioxane (8 mL) were added piperidine (97 mg, 1.14 mmol, 3 eq) and DIEA (147 mg, 1.14 mmol, 3 eq) at room temperature. The mixture was stirred at 90-91° C. under nitrogen for 15 h. LC-MS analysis showed the product peak. The mixture was not a clear solution. The mixture was concentrated to dryness and suspended in 50 mL acetonitrile containing 20% HPLC grade water. The mixture was then centrifuged at 4000 rpm for 15 min. The pellet was re-suspended in acetonitrile and centrifuged again at 4000 rpm for 15 min. The final pellet was dried under nitrogen to afford the target compound VIII (H-20) (~129 mg) as an off-white solid. LC-MS: 443.14 (M+H); $^1$H NMR (DMSO-d$_6$): 11.52 (s, 1H. NH), 9.82 (s, 1H, NH), 8.18 (s, 1H), 7.39 (m, 1H), 7.21 (m, 2H), 6.00 (s, 1H), 3.55 (m, 4H), 3.22 (s, 3H), 2.43 (s, 3H), 1.65 (m, 6H).

Example 9

Preparation of N-(2-chloro-6-methylphenyl)-2-[[2-methyl-6-(4-hydroxypiperidin-1-yl)pyrimidin-4-yl]amino]thiazole-5-carboxamide (Compound IX, H-21)

Preparation of N-(2-chloro-6-methylphenyl)-2-[[2-methyl-6-(4-hydroxypiperidin-1-yl)pyrimidin-4-yl]amino]thiazole-5-carboxamide (H-21). To a mixture of the starting material 7H (150 mg, 0.38 mmol) and dioxane (8 mL) were added 4-hydroxypiperidine (115 mg, 1.14 mmol, 3 eq) and DIEA (147 mg, 1.14 mmol, 3 eq) at room temperature. The mixture was then stirred at 90-92° C. under nitrogen for 10 h. LC-MS analysis showed the product peak. The mixture was not a clear solution. The mixture was concentrated to dryness and suspended in 50 mL acetonitrile containing 20% HPLC grade water. The mixture was then centrifuged at 4000 rpm for 15 min. The pellet was re-suspended in acetonitrile and centrifuged again at 4000 rpm for 15 min. The final pellet was dried under nitrogen to afford the target compound IX (H-21) (130 mg) as an off-white solid. LC-MS: 459.14 (M+H); $^1$H NMR (DMSO-d$_6$): 11.42 (s, 1H. NH), 9.83 (s, 1H, NH), 8.19 (s, 1H), 7.40 (m, 1H), 7.24 (m, 2H), 6.05 (s, 1H), 4.78 (s, 1H), 3.95 (m, 2H), 3.75 (m, 1H), 3.22 (s, 3H), 3.18 (m, 2H), 2.43 (s, 3H), 1.85 (m, 2H), 1.35 (m, 2H).

Example 10

Preparation of N-(2-chloro-6-methylphenyl)-2-[[2-methyl-6-((S)-3-hydroxypyrrolidin-1-yl)pyrimidin-4-yl]amino]thiazole-5-carboxamide (Compound X, H-31, 300-89)

Preparation of N-(2-chloro-6-methylphenyl)-2-[[2-methyl-6-((S)-3-hydroxypyrrolidin-1-yl)pyrimidin-4-yl]amino]thiazole-5-carboxamide (Compound XI, H-31, 300-89). To a mixture of the starting material 7H (150 mg, 0.38 mmol) and dioxane (8 mL) were added (S)-pyrrolidin-3-ol hydrochloride (141 mg, 1.14 mmol, 3 eq) and DIEA (245 mg, 1.90 mmol, 5 eq) at room temperature. The mixture was then stirred at 90-92° C. under nitrogen for 12 h. LC-MS analysis showed the product peak. The mixture was not a clear solution. The mixture was cooled to room temperature and concentrated to dryness under reduced pressure, and the resultant residue was suspended in 50 mL acetonitrile, and centrifuged at 4000 rpm for 15 min. The pellet was then suspended in cooled 80% acetonitrile, and centrifuged at 4000 rpm for 15 min. The pellet was re-suspended in cooled 80% acetonitrile, and centrifuged at 4000 rpm for 15 min. The supernatants were combined and concentrated to dryness to afford the target compound X (H-31) (105 mg) as an off-white solid. LC-MS: 445 (M+H); $^1$H NMR (DMSO-d$_6$): 11.40 (s, 1H. NH), 9.83 (s, 1H, NH), 8.19 (s, 1H), 7.40 (m, 1H), 7.24 (m, 2H), 5.80 (s, 1H), 4.98 (s, 1H), 4.35 (s, 1H), 2.53 (s, 3H), 2.20 (s, 2H), 2.12 (s, 2H), 1.85 (m, 2H).

Example 11

Preparation of N-(2-chloro-6-methylphenyl)-2-[[2-methyl-6-((R)-3-hydroxypyrrolidin-1-yl)pyrimidin-4-yl]amino]thiazole-5-carboxamide (Compound XI, H-30, 300-87)

Preparation of N-(2-chloro-6-methylphenyl)-2-[[2-methyl-6-((R)-3-hydroxypyrrolidin-1-yl)pyrimidin-4-yl]amino]thiazole-5-carboxamide (Compound X, H-30, 300-87). To a mixture of the starting material 7H (150 mg, 0.38 mmol) and dioxane (8 mL) were added (R)-pyrrolidin-3-ol (100 mg, 1.1 mmol, 3 eq) and DIEA (147 mg, 1.14 mmol, 3 eq) at room temperature. The mixture was then stirred at 90-92° C. under nitrogen for 12 h. LC-MS analysis showed the product peak. The mixture was not a clear solution. The mixture was cooled to room temperature and concentrated to dryness under reduced pressure, and the resultant residue was suspended in 50 mL acetonitrile, and centrifuged at 4000 rpm for 15 min. The pellet was then suspended in cooled 80% acetonitrile, and centrifuged at 4000 rpm for 15 min. The pellet was re-suspended in cooled 80% acetonitrile, and centrifuged at 4000 rpm for 15 min. The supernatants were combined and concentrated to dryness to afford the target compound XI (H-30) (~75 mg) as an off-white solid. LC-MS: 445 (M+H); $^1$H NMR (DMSO-d$_6$): 11.40 (s, 1H. NH), 9.83 (s, 1H, NH), 8.19 (s, 1H), 7.40 (m, 1H), 7.24 (m, 2H), 5.80 (s, 1H), 4.98 (s, 1H), 4.35 (s, 1H), 2.53 (s, 3H), 2.20 (s, 2H), 2.12 (s, 2H), 1.85 (m, 2H).

Example 12

Preparation of N-(2-chloro-6-methylphenyl)-2-[[2-methyl-6-((S)-3-aminopyrrolidin-1-yl)pyrimidin-4-yl]amino]thiazole-5-carboxamide (Compound XII, H-41, 300-93)

Preparation of N-(2-chloro-6-methylphenyl)-2-[[2-methyl-6-((S)-3-aminopyrrolidin-1-yl)pyrimidin-4-yl]amino]thiazole-5-carboxamide (H-41, 300-93). To a mixture of the starting material 7H (150 mg, 0.38 mmol) and dioxane (8 mL) were added tert-butyl (S)-pyrrolidin-3-ylcarbamate (142 mg, 0.76 mmol, 2 eq) and DIEA (147 mg, 1.14 mmol, 3 eq) at room temperature. The mixture was then stirred at 90-91° C. under nitrogen for 10 h. LC-MS analysis showed the product peak. The mixture was cooled to room temperature and concentrated under reduced pressure. After addition of methanol (4 mL), the mixture was re-concentrated to give the intermediate 300-92 as a grey solid. LC-MS: 544.12 (M+H).

To the crude sample (300-92) was added DCM (4 mL). The mixture was cooled to 5° C., and then a mixture of TFA-DCM (1:1, 5 mL) was added dropwise. After addition, the mixture was stirred at room temperature for 3 h and concentrated under reduced pressure. The residue was mixed with methanol (4 mL), followed by addition of TEA (2 mL) and stirring a while. The mixture was concentrated to dryness, then suspended in 50 mL distilled water, and centrifuged at 4000 rpm for 15 min. The pellet was re-suspended with 50 mL distilled water, and then centrifuged at 4000 rpm for 15 min. The pellet was further suspended with 100 mL 80% acetonitrile, and centrifuged at 4000 rpm for 15 min. The supernatant was evaporated to dryness to afford the target compound XII (H-41) as an off-white solid (approximately 88 mg). LC-MS: 444 (M+H); $^1$H NMR (DMSO-$d_6$): 9.83 (s, 1H, NH), 8.19 (s, 1H), 7.40 (m, 1H), 7.24 (m, 2H), 5.80 (s, 1H), 3.60-3.35 (m, 2H), 2.53 (s, 3H), 2.20 (s, 2H), 2.12 (s, 2H), 1.85 (m, 2H).

Example 13

Preparation of N-(2-chloro-6-methylphenyl)-2-[[2-methyl-6-((R)-3-aminopyrrolidin-1-yl)pyrimidin-4-yl]amino]thiazole-5-carboxamide (Compound XIII, H-40, 300-91)

Preparation of N-(2-chloro-6-methylphenyl)-2-[[2-methyl-6-((R)-3-aminopyrrolidin-1-yl)pyrimidin-4-yl]amino]thiazole-5-carboxamide (Compound XII, H-40, 300-91). To a mixture of the starting material 7H (150 mg, 0.38 mmol) and dioxane (8 mL) were added tert-butyl (R)-pyrrolidin-3-ylcarbamate (142 mg, 0.76 mmol, 2 eq) and DIEA (147 mg, 1.14 mmol, 3 eq) at room temperature. The mixture was then stirred at 90-91° C. under nitrogen for 12 h. LC-MS analysis showed the product peak. The mixture was cooled to room temperature and concentrated under reduced pressure. After addition of methanol (4 mL), the mixture was re-concentrated to give the intermediate 300-90 as a grey solid. LC-MS: 544.12 (M+H).

To the crude sample (300-90) was added DCM (4 mL). The mixture was cooled to 5° C., and then a mixture of TFA-DCM (1:1, 5 mL) was added dropwise. After addition, the mixture was stirred at room temperature for 3 h and concentrated under reduced pressure. The residue was mixed with methanol (4 mL), followed by addition of trimethylamine (TEA) (2 mL) and stirring a while. The mixture was concentrated to dryness, then suspended in 50 mL distilled water, and centrifuged at 4000 rpm for 15 min. The pellet was re-suspended with 50 mL distilled water, and then centrifuged at 4000 rpm for 15 min. The pellet was further suspended with 100 mL 80% acetonitrile, and centrifuged at 4000 rpm for 15 min. The supernatant was evaporated to dryness to afford the target compound XIII (H-40) as an off-white solid (approximately 96 mg). LC-MS: 444 (M+H); $^1$H NMR (DMSO-$d_6$): 9.83 (s, 1H, NH), 8.19 (s, 1H), 7.40 (m, 1H), 7.24 (m, 2H), 5.80 (s, 1H), 3.60-3.35 (m, 2H), 2.53 (s, 3H), 2.20 (s, 2H), 2.12 (s, 2H), 1.85 (m, 2H).

Example 14

Preparation of N-(2-chloro-6-methylphenyl)-2-[[2-methyl-6-(pyrrolidin-1-yl)pyrimidin-4-yl]amino]thiazole-5-carboxamide (Compound XIV, H-50)

Preparation of N-(2-chloro-6-methylphenyl)-2-[[2-methyl-6-(pyrrolidin-1-yl)pyrimidin-4-yl]amino]thiazole-5-carboxamide (H-50): To a mixture of the starting material 7H (300 mg, 0.76 mmol) and DMSO (10 mL) was added pyrrolidine (162 mg, 2.28 mmol, 3 eq) and DIEA (294 mg, 2.28 mmol, 3 eq) and DMAP (3 mg) at room temperature. The mixture was then heated to 110° C. under nitrogen and stirred at 110° C. for 15 h. LC-MS analysis showed the complete reaction. The mixture was concentrated to dryness, then suspended in 50 mL distilled water, and centrifuged at 4000 rpm for 15 min. The pellet was re-suspended with 50 mL distilled water, and then centrifuged at 4000 rpm for 15 min. The pellet was further suspended with 100 mL 80% acetonitrile, and centrifuged at 4000 rpm for 15 min. The supernatant was evaporated to dryness to afford the target compound XIV (H-50) as an off-white solid (approximately 314 mg). LC-MS: 429 (M+H); $^1$H NMR (DMSO-$d_6$): 11.52 (s, 1H. NH), 9.82 (s, 1H, NH), 8.18 (s, 1H), 7.39 (m, 1H), 7.21 (m, 2H), 5.79 (s, 1H), 3.35 (m, 4H), 2.39 (s, 3H), 2.23 (s, 3H), 1.90 (m, 4H).

Example 15

Protein Kinase Inhibition Studies

Off-chip Mobility Shift Assay (MSA) by Carna Biosciences, Inc (Natick, Mass.) was used for measuring the kinase activity and inhibition.

1) The 5 μL of ×4 compound solution, 5 μL of ×4 Substrate/ATP/Metal solution, and 10 μL of ×2 kinase solution were prepared with assay buffer (20 mM HEPES, 0.01% Triton X100, 2 mM DTT, pH 7.5) and mixed and incubated in a well of polypropylene 384 well microplate for 1 or 5 h (depending on kinase) at room temperature.
2) 70 μL of Termination Buffer (QuickScout Screening Assist MSA; Carna Biosciences) was added to the well.
3) The reaction mixture was applied to a LabChip system (Perkin Elmer), and the product and substrate peptide peaks were separated and quantitated.
4) The kinase reaction was evaluated by the product ratio calculated from peak heights of product (P) and substrate (S) peptides (P/(P+S)).
5) The reaction conditions were followed according to assay protocols of Carna Biosciences, Inc (BMA 3F, 1-5-5 Minatojima-Minamimachi, Chuo-ku, Kobe 650-0047, Japan; www.carnabio.com).
6) Data analysis: The readout value of reaction control (complete reaction mixture) was set as a 0% inhibition, and the readout value of background (Enzyme (−)) was set as a 100% inhibition, then the percent inhibition of each test solution was calculated.

Compound I showed >50% inhibition at 1 nM on the following recombinant kinases: ABL, ABL(E255K), ACK, ARG, BLK, BMX, BTK, DDR2, EPHA1, FGR, FMS, FRK, FYN(isoform a), HCK, LCK, LYNa, PDGFRα, PDGFRβ, SRC, YES. Compound I showed concentration-dependent inhibition of recombinant BTK, ACK and PDGFRα activity with an $IC_{50}$ of approximately 0.2, 0.5 and 1.4 nM, respectively. Compound I inhibited recombinant PIK3CA/PIK3R1 activity with an IC50 of approximately 12 nM.

Compound I showed >50% inhibition at 10 nM on the following recombinant kinases: YES, FRK, SRC, LYNa, FMS, BMX, ABL, FYN(isoform b), FGR, HCK, FYN (isoform a), LCK, DDR2, ARG, ABL(E255K), BTK, EPHA1, BLK, ACK, SRM, PDGFRβ, PIK3CA/PIK3R1, PDGFRα, CSK, KIT(D816V), KIT(D816Y), BRK.

Compound I showed <50% inhibition at 10 nM on the following recombinant kinases: PDGFRα(V561D), DDR1, KIT, KIT(V560G), HER4, KIT(D816E), EGFR(L858R), KIT(V654A), PDGFRα(D842V), EGFR, EGFR(L861Q), EGFR(d746-750), JAK1, RET, RET(S891A), FGFR3, ALK, WNK3, RET(Y791F), BRAF(V600E), RAF1, ROCK1, AurA, MAP2K2, RET(M918T), KDR, FGFR2, Erk1, EGFR(T790M), RET(G691 S), PDGFRα(T674I), p38α, HER2, JAK3, MAP2K1, p38β, EGFR(T790M/L858R), FLT1, BRAF, KIT(T670I), MET, skMLCK, MNK1, MST1, PKD1, JAK2, YES(T348I), FGFR1, EGFR (d746-750/T790M).

Compound II showed >50% inhibition at 1 nM on the following recombinant kinases: SRC, YES, LCK, HCK, BTK, LYNa, FRK, FYN(isoform a), FYN(isoform b), TEC, BMX, LYNb, ABL, FGR, FMS, BLK, EPHA1, ABL (E255K). Compound II showed <50% inhibition at 1 nM on the following recombinant kinases: PDGFRβ, PDGFRα, PIK3CA/PIK3R1, KIT, KIT(V560G), EGFR, HER2, YES (T348I), ITK, p38α, ABL(T315I), RAF1, p38β, BRAF. Compound II showed concentration-dependent inhibition of recombinant BTK activity with an $IC_{50}$ of <1 nM.

Compound II showed >50% inhibition at 10 nM on the following recombinant kinases: BTK, PDGFRβ, KIT (V560G), PDGFRα, KIT. Compound II showed <50% inhibition at 10 nM on the following recombinant kinases: PIK3CA/PIK3R1, EGFR, p38α, RAF1, HER2, p38β, BRAF.

Compound II showed >50% inhibition at 100 nM on the following recombinant kinases: PDGFRα, KIT(V560G), KIT, PDGFRβ, EGFR. Compound II showed <50% inhibition at 100 nM on the following recombinant kinases: p38α, RAF1, PIK3CA/PIK3R1, HER2, p38β, BRAF.

Compound IV showed >50% inhibition at 1 nM on the following recombinant kinases: SRC, YES, LCK, HCK, BTK, LYNa, TEC, BMX, ABL, ABL (E255K).

Compound V showed >50% inhibition at 1 nM on the following recombinant kinases: SRC, YES, LCK, HCK, BTK, LYNa, TEC, BMX, ABL, ABL (E255K).

Compound VI showed >50% inhibition at 1 nM on the following recombinant kinases: SRC, YES, LCK, HCK, BTK, LYNa, TEC, BMX, ABL, ABL (E255K).

Compound VII showed >50% inhibition at 1 nM on the following recombinant kinases: SRC, YES, LCK, HCK, BTK, LYNa, TEC, BMX, ABL, ABL (E255K).

Compound VIII showed >50% inhibition at 1 nM on the following recombinant kinases: SRC, YES, LCK, HCK, BTK, LYNa, TEC, BMX, ABL, ABL (E255K).

Compound IX showed >50% inhibition at 1 nM on the following recombinant kinases: SRC, YES, LCK, HCK, BTK, LYNa, TEC, BMX, ABL, ABL (E255K).

Compound X showed >50% inhibition at 1 nM on the following recombinant kinases: SRC, YES, LCK, HCK, BTK, LYNa, TEC, BMX, ABL, ABL (E255K). Compound X showed concentration-dependent inhibition of recombinant ABL, ABL (E255K), BTK and BTK (C481S) activity with $IC_{50}$ values of <1 nM, respectively.

Compound XI showed >50% inhibition at 1 nM on the following recombinant kinases: SRC, YES, LCK, HCK, BTK, LYNa, TEC, BMX, ABL, ABL (E255K). Compound XI showed concentration-dependent inhibition of recombinant ABL, ABL (E255K), BTK and BTK (C481S) activity with $IC_{50}$ values of <1 nM, respectively.

Compound XII showed >50% inhibition at 1 nM on the following recombinant kinases: SRC, YES, LCK, HCK, BTK, LYNa, TEC, BMX, ABL, ABL (E255K).

Compound XIII showed >50% inhibition at 1 nM on the following recombinant kinases: SRC, YES, LCK, HCK, BTK, LYNa, TEC, BMX, ABL, ABL (E255K).

Example 16

Cell Inhibition Assay

Cell lines of SU-DHL-4 (ATCC® CRL-2957™), K-562 (ATCC® CCL-243™), and Mino (ATCC® CRL-3000™) were purchased from American Type Culture Collection (ATCC, Manassas, Va.). SU-DHL-4 cells and Mino cells grew in ATCC-formulated RPMI-1640 medium (ATCC) supplemented with 10% fetal bovine serum (FBS) (Gibco, Life Technologies) (complete medium) a T-75 flask at 37° C. under 5% $CO_2$ with saturated humidity. K-562 cells grew in ATCC-formulated Iscove's Modified Dulbecco's Medium (IMDM) supplemented with 10% FBS (Gibco, Life Technologies) (complete medium) a T-75 flask at 37° C. under 5% $CO_2$ with saturated humidity. When the cells grew to a concentration of approximately $1 \times 10^6$ cells/mL, they were diluted to $2.5-5 \times 10^4$ cells/mL with the corresponding complete medium for each cell line. A 200 μL aliquot of the cell suspension was added to the well of a 96-well plate which was pre-added with 1 μL of the test compounds at various concentrations, and the plate was incubated at 37° C. under 5% $CO_2$ with saturated humidity for 48 h. At end of the cell culture, a 10 μL aliquot of PrestoBlue® Cell Viability reagent (ThermoFisher Scientific) was added into the well, and the plate was incubated at 37° C. for approximately 60 min. The absorptions at 570 and 600 nm were measured with a SpectraMaxMicroplate reader (Molecular Devices). The absorbance at 570 nm was normalized to that at 600 nm. The normalized absorbance at 570 nm was used for $IC_{50}$ calculation following the median-effect plot method (TC Chou. Theoretical basis, experimental design, and computerized simulation of synergism and antagonism in drug combination studies. Pharmacol Rev. 2006; 58:621-681).

Compounds I, II, III, IV, V, VI, VII, VIII, IX, X, XI, XII, XIII, and XIV showed concentration-dependent inhibition of growth of SU-DHL-4 with $IC_{50}$ values of <15 nM, respectively.

Compounds I, II, III, IV, V, VI, VII, VIII, IX, X, XI, XII, XIII, and XIV showed concentration-dependent inhibition of growth of K562 cells with $IC_{50}$ values of <2 nM, respectively.

Compounds I, II, III, IV, V, VI, VII, VIII, IX, X, XI, XII, XIII and XIV showed concentration-dependent inhibition of growth of Mino with $IC_{50}$ values of <50 nM, respectively.

Example 17

Metabolic Stability

Metabolic stability in liver microsomes: test compounds and dasatinib were incubated at a concentration of 1 μM in human liver microsomes (0.5 mg/mL) (Corning Inc., Tewksbury, Mass.) in 0.1 M phosphate buffer containing 10 mM $MgCl_2$, 1 mM NADPH and 2 mM UDPGA for time points ranging from zero to 60 min at 37° C. (see FIG. 1). Dasatinib (HY10181/CS0100, 302962-49-8, Batch No: 13044) was purchased from MedChemExpress USA (Monmouth Junction, N.J.). The incubation reactions at various time points were quenched by adding 2× volumes of acetonitrile containing 100 nM reserpine. The quenched incubation samples were centrifuged at 4000 RPM for 10 min, and the supernatants injected for LC/MS/MS analysis. LC/MS/MS analysis was carried out on a AB Sciex 4000 Q Trap LC/MS/MS system coupled with Shimadzu Prominence UFLCXR 20 series (including a CBM-20A controller, two LC-20ADXR solvent delivery units, SIL-20AC HT autosampler, CTO-20A column oven, and a SPD-20A UV detector). The samples were separated on a Phenomenex Columbus column (C18, 4 μm, 50×2 mm) eluted with two solvent systems: 2 mM ammonium acetate in water containing 0.1% formic acid (A) and methanol (B) at a linear gradient starting with 25% B. Electrospray ionization in positive mode was used to acquire LC/MS/MS data. The in vitro t½ and intrinsic clearance were calculated using method previous reported (Obatch S. Prediction of human clearance of twenty-nine drugs from hepatic microsomal intrinsic clearance data: An examination of in vitro half-life approach and nonspecific binding to microsomes. Drug Metab Dispos. 1999; 27(11):1350-9).

Example 18

Pharmacokinetics

Pharmacokinetics: Compound IV and dasatinib (2-in-1) were both dissolved at a concentration of 0.2 mg/mL (each compound) in water containing 2.5% DMSO, 20% propylene glycol 300, and 8% dextrose solution (50%) for intravenous dosing, and at a concentration of 0.25 mg/mL (each compound) in water containing 5% DMSO, 20% propylene glycol 300, and 10% dextrose solution (50%) for oral dosing. Compound V and compound III (2-in-1) were both dissolved at a concentration of 0.2 mg/mL (each compound) in water containing 2.5% DMSO, 20% propylene glycol 300, and 8% dextrose solution (50%) for intravenous dosing, and at a concentration of 0.25 mg/mL (each compound) in water containing 5% DMSO, 20% propylene glycol 300, and 10% dextrose solution (50%) for oral dosing. Compound X and dasatinib (2-in-1) were both dissolved at a concentration of 0.2 mg/mL (each compound) in water containing 2.5% DMSO, 30% propylene glycol 300 and 10% dextrose solution (50%) for intravenous dosing, and at a concentration of 0.5 mg/mL (each compound) in water containing 5% DMSO, 50% propylene glycol 300, and 10% Solutol® HS 15 (Sigma-Aldrich) for oral dosing. Compound XI and compound III (2-in-1) were both dissolved at a concentration of 0.2 mg/mL (each compound) in water containing 2.5% DMSO, 30% propylene glycol 300, and 10% dextrose solution (50%) for intravenous dosing and at a concentration of 0.5 mg/mL (each compound) in water containing 5% DMSO, 50% propylene glycol, and 10% Solutol® HS 15 for oral dosing.

Sprague-Dawley rats (approximate weight 275-300 g, N=3) were dosed intravenously at 5 mL/kg and orally at 10 mL/kg with the above dosing solutions. Blood samples were collected into tubes containing EDTA as the anticoagulant at 0, 0.25 (intravenous only), 0.5, 1, 2, 4, 8, 10, and 24 h post-dosing, and plasma samples were prepared by centrifugation. The plasma samples were mixed with 3× volumes of acetonitrile containing 100 nM reserpine as the internal standard, and centrifuged at 4000 RPM for 15 min. The supernatants were injected for LC/MS analysis which were carried out on a AB Sciex 4000 Q Trap LC/MS/MS system coupled with Shimadzu Prominence UFLCXR 20 series (including a CBM-20A controller, two LC-20ADXR solvent delivery units, SIL-20AC HT autosampler, CTO-20A column oven, and a SPD-20A UV detector). The samples were separated on a Phenomenex Columbus column (C18, 4 μm, 50×2 mm) eluted with two solvent systems: 2 mM ammonium acetate in water containing 0.1% formic acid (A) and methanol (B) at a linear gradient starting with 25% B. Electrospray ionization in positive mode was used to acquire LC/MS/MS data. Plasma concentrations of compounds III, IV, V, X, XI and dasatinib were quantitated using standard curves, respectively.

Example 19

Tissue Distribution

Lung Tissue and Plasma Concentration Ratios: Compound X and dasatinib (2-in-1) were both dissolved at a concentration of 0.5 mg/mL (each compound) in water containing 5% DMSO, and 50% propylene glycol 300, and 9% Solutol® HS 15. Compound XI and dasatinib (2-in-1) were both dissolved at a concentration of 0.5 mg/mL (each compound) in water containing 5% DMSO, 20% propylene glycol 300.

CD-1 mouse (approximate weight 30 g, N=3) were dosed by oral gavage at 10 mL/kg. Blood samples were collected into tubes containing EDTA as the anticoagulant at 1, 2, 4, 10 h post-dosing for Compound X, and predose, 1, 2, 3, 8, 10 and 24 h post-dosing for Compound XI. The plasma samples were prepared by centrifugation. Lung samples were also collected at each of the above time points. The lung samples were homogenated in 4× distilled water (v/w). The plasma samples and the homogenated lung tissue samples were mixed with 3× volumes of acetonitrile containing 100 nM reserpine as the internal standard, and centrifuged at 4000 RPM for 15 min. The supernatants were injected for LC/MS analysis which were carried out on a AB Sciex 4000 Q Trap LC/MS/MS system coupled with Shimadzu Prominence UFLCXR 20 series (including a CBM-20A controller, two LC-20ADXR solvent delivery units, SIL-20AC HT autosampler, CTO-20A column oven, and a SPD-20A UV detector). The samples were separated on a Phenomenex Columbus column (C18, 4 μm, 50×2 mm) eluted with two solvent systems: 2 mM ammonium acetate in water containing 0.1% formic acid (A) and methanol (B) at a linear gradient starting at 25%. Electrospray ionization in positive mode was used to acquire LC/MS/MS data. The plasma and tissue concentrations of Compounds X, XI and dasatinib were determined using standard curves, respectively.

It is understood that the examples and embodiments described herein are for illustrative purposes only and that various modifications or changes in light thereof will be suggested to persons skilled in the art and are to be included within the spirit and purview of this application and scope of appended claim. All publications, patents, and patent applications cited herein are hereby incorporated by reference.

I claim:

1. A compound having the structure

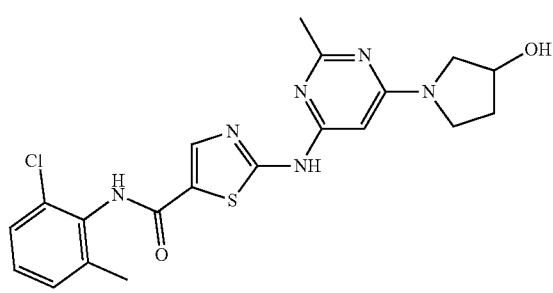 [SMILES: Cc1nc(Nc2ncc(C(=O)Nc3c(C)cccc3Cl)s2)cc(N2CCC(O)C2)n1]

and/or a salt, enantiomer or enantiomeric mixture thereof.

2. A compound according to claim 1 having the structure of compound X:

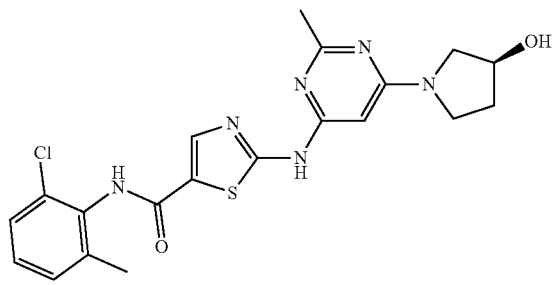

compound X and/or a salt thereof.

3. A compound according to claim 1 having the structure of compound XI:

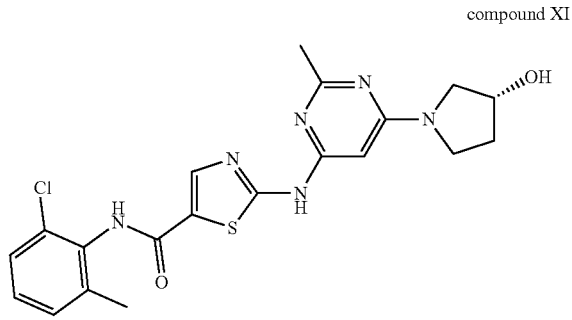 [SMILES: Cc1nc(Nc2ncc(C(=O)Nc3c(C)cccc3Cl)s2)cc(N2CC[C@@H](O)C2)n1]

compound XI and/or a salt thereof.

4. A pharmaceutical composition comprising a compound having the structure

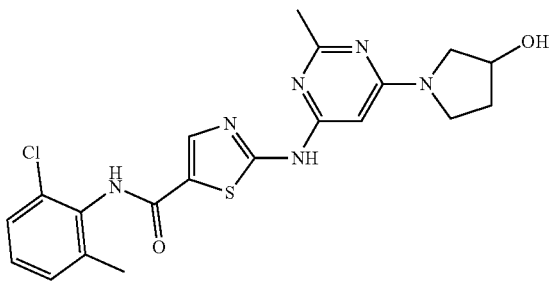 [SMILES: Cc1nc(Nc2ncc(C(=O)Nc3c(C)cccc3Cl)s2)cc(N2CCC(O)C2)n1]

and/or a salt, enantiomer or enantiomeric mixture thereof, and a pharmaceutically acceptable excipient, carrier and/or diluent.

5. The pharmaceutical composition of claim 4, wherein said compound is compound X:

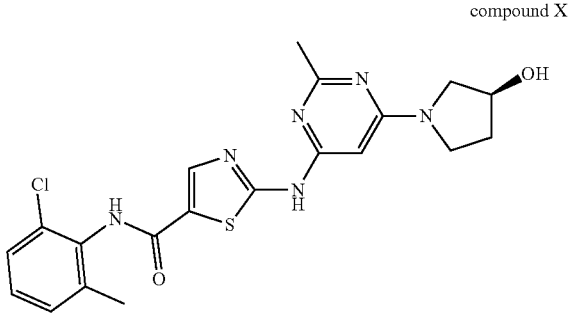 [SMILES: Cc1nc(Nc2ncc(C(=O)Nc3c(C)cccc3Cl)s2)cc(N2CC[C@H](O)C2)n1]

compound X and/or a salt thereof.

6. The pharmaceutical composition of claim 4, wherein said compound is compound XI:

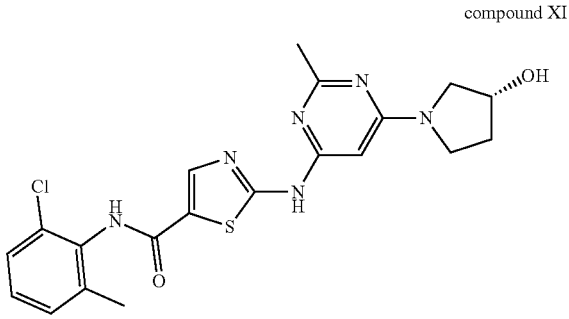 [SMILES: Cc1nc(Nc2ncc(C(=O)Nc3c(C)cccc3Cl)s2)cc(N2CC[C@@H](O)C2)n1]

compound XI and/or a salt thereof.

7. A compound of formula

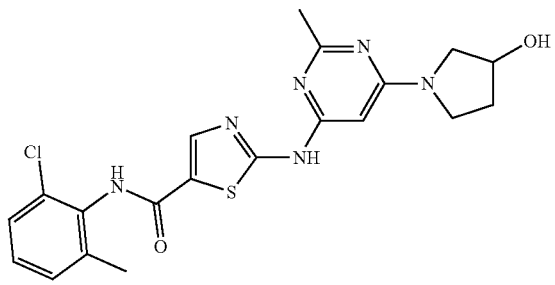 [SMILES: Cc1nc(Nc2ncc(C(=O)Nc3c(C)cccc3Cl)s2)cc(N2CCC(O)C2)n1]

and/or a pharmaceutically acceptable salt thereof.

8. A pharmaceutical composition comprising the compound of claim 7 and/or pharmaceutically acceptable salt thereof, and pharmaceutically acceptable excipient.

9. A pharmaceutical composition comprising the compound of claim 7, and further comprising pharmaceutically acceptable excipient.

10. A compound of formula

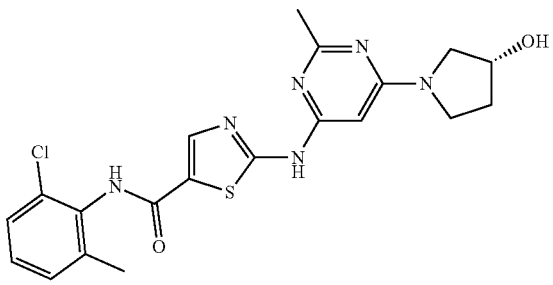 [SMILES: Cc1nc(Nc2ncc(C(=O)Nc3c(C)cccc3Cl)s2)cc(N2CC[C@@H](O)C2)n1]

and/or a pharmaceutically acceptable alts salt thereof.

11. A pharmaceutical composition comprising the compound of claim 10 and/or pharmaceutically acceptable salt thereof, and pharmaceutically acceptable excipient.

12. A pharmaceutical composition comprising the compound of claim 10, and further comprising pharmaceutically acceptable excipient.

* * * * *

UNITED STATES PATENT AND TRADEMARK OFFICE
CERTIFICATE OF CORRECTION

PATENT NO. : 10,174,018 B2  
APPLICATION NO. : 15/839332  
DATED : January 8, 2019  
INVENTOR(S) : Kan He Page 1 of 1

It is certified that error appears in the above-identified patent and that said Letters Patent is hereby corrected as shown below:

In the Claims

Claim 7, Column 57, Lines 2-14, replace the chemical formula:

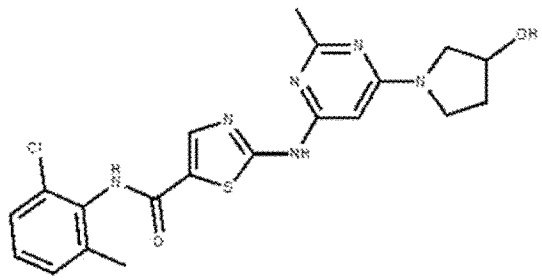

With the chemical formula:

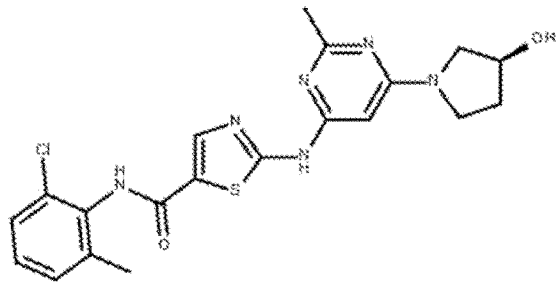

Signed and Sealed this  
Fourteenth Day of December, 2021

Drew Hirshfeld  
*Performing the Functions and Duties of the  
Under Secretary of Commerce for Intellectual Property and  
Director of the United States Patent and Trademark Office*